(12) United States Patent
Takahashi et al.

(10) Patent No.: US 7,371,877 B2
(45) Date of Patent: May 13, 2008

(54) GLYCEROL ESTER DERIVATIVE

(75) Inventors: Kazunobu Takahashi, Kanagawa (JP);
Hiroshi Kitaguchi, Kanagawa (JP);
Kazuhiro Aikawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 136 days.

(21) Appl. No.: 10/507,486

(22) PCT Filed: Mar. 27, 2003

(86) PCT No.: PCT/JP03/03814

§ 371 (c)(1),
(2), (4) Date: Sep. 13, 2005

(87) PCT Pub. No.: WO03/080554

PCT Pub. Date: Oct. 2, 2003

(65) Prior Publication Data
US 2006/0062726 A1 Mar. 23, 2006

(30) Foreign Application Priority Data
Mar. 27, 2002 (JP) .............................. 2002-088694
Mar. 27, 2002 (JP) .............................. 2002-088695

(51) Int. Cl.
C07F 9/02 (2006.01)
A61K 51/04 (2006.01)
(52) U.S. Cl. .......................... 554/79; 534/10; 424/1.21; 558/180
(58) Field of Classification Search ................. 554/81, 554/79; 424/1.21; 534/11, 10; 558/179, 558/180
See application file for complete search history.

(56) References Cited

U.S. PATENT DOCUMENTS 4,873,075 A 10/1989 Longino et al.
6,103,216 A 8/2000 Bakan et al.

FOREIGN PATENT DOCUMENTS

EP 0 037 583 A 10/1981

OTHER PUBLICATIONS

Weichert J P et al: "Polyiodinated Triglyceride Analogs as Potential Computed Tomography Imaging Agents for the Liver" Journal of Medicinal Chemistry, American Chemical Society. Washington, US, vol. 38, No. 4, Feb. 17, 1995, pp. 636-646, XP001057012.
Weichert J P et al. : "Combined Hepatocyte-selective and Blood-Pool Contrast Agents for the CT Detection of Experimental Liver Tumors in Rabbits," RADIOLOGY, vol. 216, No. 3, 2000, pp. 865-871, XP002244766.
K. Bhardwaj et al. : "Identification, Purification and Characterization of a Thermally Stable Lipase from Rice Bran. A New Member of the (Phospho) Lipase Family", Plant Physiology, vol. 127, No. 4, 2001, pp. 1728-1738, XP002244767.
J. P . Weichert et al.. : "Potential Tumor-or Organ-Imaging Agents." Journal of Medicinal Chemistry, vol. 29, No. 12, 1986, pp. 2457-2465, XP002244768.
Database Caplus 'Online! Chemical Abstracts Service, Columbus, Ohio, US; 1986, J. P. Weichert et al. : "Polyiodinated Triglyceride Analogs As Potential Hepatic Imaging Agents" Database accession No. 1986: 530036, XP002244769.
Database Caplus 'Online! Chemical Abstracts Service, Columbus, Ohio, US; 2000 J. P. Weichert et al. : "Polyiodinated triglyceride lipid emulsions for use as hepatoselective contrast agents in CT: effects of physicochemical properties on biodistribution and imaging profiles" Database accession No. 2000: 205019 XP002244770.
Database Caplus 'Online! Chemical Abstracts Service, Columbus, Ohio, US; 1992 Schwendner S. W. et al. : "Potential organ or tumor imaging agents" Database accession No. 1992:587410, XP002244771.
Database Medline 'Onl ine! US National Library of Medicine (NLM), Bethesda, MD, US; 1993 FF Knapp et al. : "Site-specific stable radioiodination of 1,2-Pal-3-IPPA: an agent for t he potential clinical evaluation of pancreatic insufficiency by urine analysis" Database accession No. 93286735, XP002244772.

(Continued)

Primary Examiner—Sreenivasan Padmanabhan
Assistant Examiner—Nathan W. Schlientz
(74) Attorney, Agent, or Firm—Sughrue Mion, PLLC

(57) ABSTRACT

A compound represented by the following general formula (IA) or a salt thereof:

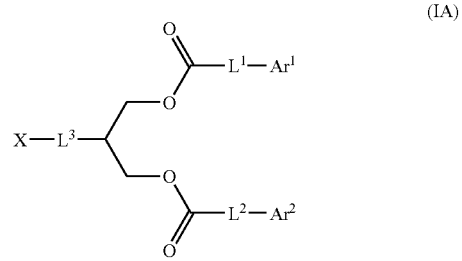

wherein $Ar^1$ represents hydrogen atom or an aryl group having at least one iodine atom as a substituent; $Ar^2$ represents an aryl group having at least one iodine atom as a substituent; $L^1$ and $L^2$ independently represent a divalent bridging group of which main chain contains 6 or more carbon atoms; $L^3$ represents a single bond or a divalent bridging group of which main chain contains 1 to 6 carbon atoms and one oxygen atom; X represents a functional group containing at least one heteroatom, provided that, when $L^3$ is a single bond, X represents a functional group other than hydroxyl group. The compound can be used as a membrane component of liposomes, and the liposomes can be used as a contrast medium for X-ray radiography.

7 Claims, 8 Drawing Sheets

OTHER PUBLICATIONS

M-L Alcaraz et al.: "Synthesis and Properties of Photoactivatable Phospholipid Derivatives Designed To Probe the Membrane-Associate Domains of Proteins". Journal of Organic Chemistry, vol. 61, 1996, pp. 192-201, XP002250373.

B. Corsico et al. : "Evidence for a central apolipoprotein A-I domain loosely bound to lipids in discoidal lipoproteins that us capable of penetrating the bilayer of phospholipid vesicles". Journal of Biological Chemistry, vol. 276, No. 20, 2001, pp. 16978-16985, XP002250374.

Y. Ogawa et al. : "Regioselective photolabeling of glycoprotein A in membranes". Chem. Eur. Journal, vol. 8, No. 8, 2002, pp. 1843-1849, XP002250375.

GLYCEROL ESTER DERIVATIVE

TECHNICAL FIELD

The present invention relates to a glycerol ester derivative. More specifically, the present invention relates to a glycerol ester derivative which is a 1,3-diacylglyceride compound having one or more iodophenyl groups, of which 2-hydroxyl group is substituted with a functional group containing a heteroatom. The present invention also relates to a glycerophosphoric acid ester derivative. More specifically, the present invention relates to a 1,3-diacyl-2-phosphoglyceride compound and 2,3-diacyl-1-phosphoglyceride compound having an iodophenyl group. These compounds can be used as membrane components of liposomes, and these liposomes can be used as a contrast medium for X-ray radiography.

BACKGROUND ART

In the field of X-ray radiography using an iodine compound, for example, X-ray angiography, a technique is available which comprises administration of a water-soluble iodine-containing contrast medium for visualization of vascular flows, and detection of lesions at which the flows are obstructed. However, in the aforementioned method, the iodine-containing contrast medium is present in the vascular flows to detect changes of vascular flows inside the vessels, and the method has difficulty in distinguishing the lesions from normal tissues as compared to a method wherein an iodine-containing contrast medium is present in cells consisting a lesion. For this reason, by the above method, only a lesion where constriction progresses 50% or more can be detected, and it is difficult to detect a lesion before the onset of attack of an ischemic disease.

Separately, attempts have also been reported in which a hydrophobic iodine-containing contrast medium or a hydrophilic contrast medium is formulated for selective accumulation in a target lesion (International Patent Publications WO95/19186, WO95/21631, WO89/00812, British Patent No. 867650, WO96/00089, WO94/19025, WO96/40615, WO95/2295, WO98/41239, WO98/23297, WO99/02193, WO97/06132, U.S. Pat. Nos. 4,192,859, 4,567,034, 4,925, 649, Pharm. Res., 6 (12), 1011 (1989); Pharm. Res., 16 (3), 420 (1999); J. Pharm. Sci., 72 (8), 898 (1983); Invest. Radiol., 18 (3), 275 (1983)). For example, Pharm. Res., 6 (12), 1011 (1989) discloses that injection of an oil-particle dispersion of cholesteryl iopanoate as a hydrophobic compound allows accumulation of the iodine compound in arteriosclerotic lesions of experimental animals. Further, Pharm. Res., 16 (3), 420 (1999) discloses that administration of cholesteryl iopanoate after being taken up into acetyl-LDL allows accumulation of the iodine compound in arteriosclerotic lesions of experimental animals.

J. Pharm. Sci. 72 (8), 898 (1983) discloses examples of X-ray hepatography and splenography by injection of an oil-particle dispersion of cholesteryl iopanoate. U.S. Pat. No. 4,567,034 discloses a method of selective hepatography or splenography utilizing liposomes encapsulating an ester of diatrizoic acid. International Patent Publications WO96/28414 and WO96/00089 disclose contrast media for imaging vascular pools or lymphatic systems. However, the methods using these formulations are not satisfactory in efficiency and selectivity for a purpose of selective contrast of vascular diseases, and no example is reported in which vascular diseases are imaged by utilizing X-ray irradiation.

International Publication WO01/93918 discloses an example of radiography of arteriosclerotic lesions, wherein a hydrophobic and hydrolysis-resistant radioactive iodine-containing contrast medium is formulated into a microemulsion or allowed to be taken up into acetyl-LDL and then administered to experimental animals. Further, it is also reported that the aforementioned cholesteryl iopanoate is not degraded in living bodies and accumulated in organs in vivo, in particular, livers [J. Med. Chem., 25, 1500 (1982)]. These properties of the compounds indicate that the compounds remain in living bodies for a prolonged period of time, and the properties are not favorable when diagnostic use such as X-ray contrast media is desired.

From a viewpoint of intended use of chemical compounds, methods have been reported in which a triglyceride compound comprising an alkylcarboxylic acid formed by two of 3-amino-2,4,6-triiodophenyl groups and a saturated/unsaturated fatty acid is formulated as an oil particle dispersion (lipid emulsion) or a Tween 20 dispersion and used for the purpose of hepatography or imaging of blood-pool (Radiology, 216 (3) 865 (2000); Invest. Radiol., 35 (3), 158 (2000); International Patent Publication WO98/46275; J. Pharm. Sci., 85 (9), 908 (1996); Pharm. Res., 13 (6), 875 (1996); International Patent Publication WO95/31181; J. Med. Chem., 38 (4), 636 (1995); Invest. Radiol., 29 (SUPPL. 2), S284 (1994); International Patent Publication WO94/19025; U.S. Pat. No. 4,873,075; Appl. Radiol. Isot., 37 (8), 907 (1986); J. Med. Chem., 29 (12), 2457 (1986)). Further, U.S. Pat. No. 4,873,075 and J. Med. Chem., 29 (12), 2457 (1986) mentioned above describe diacyl-1,3-glyceride compounds comprising an alkylcarboxylic acid containing two of 3-amino-2,4,6-triiodophenyl groups and oxidized compounds thereof. However, a use thereof other than as synthetic intermediates is not described. Moreover, the 2-position of the glycerin moiety is unsubstituted, and the compounds have no structurally characteristic functional group.

Phosphoric acid esters of diacylglyceride compounds comprising a saturated/unsaturated long chain fatty acid, in particular, those compound of which 1-position is esterified with phosphoric acid, are found as a membrane component of organisms, and therefore, various derivatives thereof have been known. However, most of these compounds are phosphoric acid ester compounds comprising an unsubstituted saturated/unsaturated fatty acid. In particular, compounds having an iodophenyl group in the structures are described in J. Amer. Chem. Soc., 117 (11), 3084 (1995); J. Org. Chem., 61 (1), 192 (1996); Eur. J. Org. Chem., 10, 2563 (1999); Tetrahedron Lett., 41 (35), 6737 (2000) and the like. However, these compounds have only one monoiodophenyl group in their structures. Although Tetrahedron Lett., 27 (3), 271 (1986) describes compounds having tyroxine, the bonding position of the tyroxine moiety is not in the aliphatic acid moiety, but at the end of the phosphoric acid ester moiety, and therefore their structural characteristic is totally different from that of the compounds of the present invention.

DISCLOSURE OF THE INVENTION

An object of the present invention is to provide an iodine compound suitable for an iodine-containing contrast medium in a form of a liposome, which enables lesion-selective contrast radiography. The inventors of the present invention conducted researches to achieve the foregoing object. As a result, they found that a 1,3-diacylglyceride having an iodophenyl group which is introduced with a functional group containing a heteroatom at the 2-position, as well as a 1,3-diacyl-2-phosphoglyceride compound and 2,3-diacyl-1-phosphoglyceride compound having an iodophenyl group had superior properties as a membrane component of liposomes for a contrast medium for X-ray radiography, and that a lesion of an vascular disease was selectively contrasted by X-ray radiography using the liposomes. They also found that the compounds had a property that they were metabolized in the liver after the radiography and not accumulated in living bodies. The present invention was achieved on the basis of the above findings.

The present invention thus provides a compound represented by the following general formula (IA) or a salt thereof:

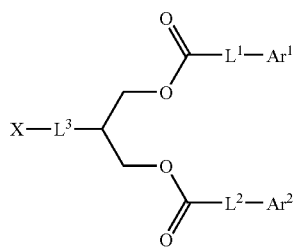
(IA)

(in the formula, $Ar^1$ represents hydrogen atom or an aryl group having at least one iodine atom as a substituent; $Ar^2$ represents an aryl group having at least one iodine atom as a substituent; $L^1$ and $L^2$ independently represent a divalent bridging group of which main chain contains 6 or more carbon atoms; $L^3$ represents a single bond or a divalent bridging group of which main chain contains 1 to 6 carbon atoms and one oxygen atom; X represents a functional group containing at least one heteroatom, provided that, when $L^3$ is a single bond, X represents a functional group other than hydroxyl group).

According to preferred embodiments of the aforementioned invention, there are provided the aforementioned compound or a salt thereof, wherein $Ar^2$ is a phenyl group having at least three iodine atoms as substituents; the aforementioned compound or a salt thereof, wherein $Ar^1$ is an aryl group having at least one iodine atom as a substituent; and the aforementioned compound or a salt thereof, wherein $Ar^1$ and $Ar^2$ independently represent a phenyl group having at least three iodine atoms as substituents.

According to further preferred embodiments, there are provided the aforementioned compound or a salt thereof, wherein X is a group represented by the following general formula (IIA):

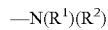

(in the formula, $R^1$ and $R^2$ independently represent hydrogen atom, an alkyl group having 1 to 10 carbon atoms which may be substituted, or an acyl group having 1 to 10 carbon atoms which may be substituted, and $R^1$ and $R^2$ may bind to each other to form a ring) or a group represented by the following general formula (IIIA):

(in the formula, $R^3$ represents hydrogen atom, an alkyl group having 1 to 10 carbon atoms which may be substituted, or an acyl group having 1 to 10 carbon atoms which may be substituted); and the aforementioned compound or a salt thereof, wherein $R^3$ is hydrogen atom or an alkyl group having 1 to 10 carbon atoms and having at least one substituent selected from the group consisting of an alkoxyl group, hydroxyl group and an amino group.

The present invention also provides a compound represented by the following general formula (IB) or a salt thereof:

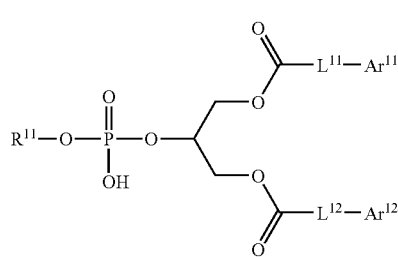
(IB)

(in the formula, $Ar^{11}$ and $Ar^{12}$ independently represents hydrogen atom or an aryl group having at least one iodine atom as a substituent, provided that $Ar^{11}$ and $Ar^{12}$ do not simultaneously represent hydrogen atom; $L^{11}$ and $L^{12}$ independently represent a divalent bridging group of which main chain contains 6 or more carbon atoms; $R^{11}$ represents hydrogen atom or an alkyl group having two or more carbon atoms and having a functional group containing at least one heteroatom as a substituent).

According to preferred embodiments of the above invention, there are provided the aforementioned compound or a salt thereof, wherein $Ar^{11}$ is a phenyl group having at least three iodine atoms as substituents; the aforementioned compound or a salt thereof, wherein $Ar^{11}$ and $Ar^{12}$ independently represent an aryl group having at least one iodine atom as a substituent; and the aforementioned compound or a salt thereof, wherein $Ar^{11}$ and $Ar^{12}$ independently represent a phenyl group having at least three iodine atoms as substituents.

The present invention also provides a compound represented by the following general formula (IIB) or a salt thereof:

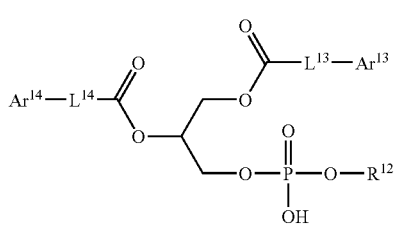
(IIB)

(in the formula, $Ar^{13}$ and $Ar^{14}$ independently represents hydrogen atom or an aryl group having at least one iodine atom as a substituent, provided that $Ar^{13}$ and $Ar^{14}$ do not simultaneously represent hydrogen atom; $L^{13}$ and $L^{14}$ independently represent a divalent bridging group of which main chain contains 6 or more carbon atoms; $R^{12}$ represents hydrogen atom or an alkyl group having two or more carbon atoms and having a functional group containing at least one heteroatom as a substituent).

According to preferred embodiments of the above invention, there are provided the aforementioned compound or a salt thereof, wherein at least one of $Ar^{13}$ and $Ar^{14}$ represents a phenyl group having at least three iodine atoms as substituents; the aforementioned compound or a salt thereof, wherein $Ar^{13}$ and $Ar^{14}$ independently represent an aryl group having at least one iodine atom as a substituent; and the aforementioned compound or a salt thereof, wherein $Ar^{13}$ and $Ar^{14}$ independently represent a phenyl group having at least three iodine atoms as substituents.

As another aspect, the present invention provides a liposome, which contains any of the aforementioned compounds or a salt thereof as a membrane component. According to a preferred embodiment thereof, there is provided the aforementioned liposome, which contains a phosphatidylcholine and a phosphatidylserine as membrane components.

The present invention further provides a contrast medium for X-ray radiography, which comprises the aforementioned liposome. As preferred embodiments of this invention, provided are the aforementioned contrast medium for X-ray radiography, which is used for radiography of a vascular disease; the aforementioned contrast medium for X-ray radiography, which is used for radiography of vascular smooth muscle cells which are abnormally proliferated under an influence of foam macrophages; the aforementioned contrast medium for X-ray radiography, which is used for radiography of a tissue or lesion where macrophages localize; the aforementioned contrast medium for X-ray radiography, wherein the tissue where macrophages localize is selected from the group consisting of liver, spleen, air vesicle, lymph node, lymph vessel, and renal epithelium; and the aforementioned contrast medium for X-ray radiography, wherein the lesion where macrophages localize is selected from the group consisting of lesions of tumor, inflammation, and infection.

The present invention further provide use of any one of the aforementioned compounds or a salt thereof for manufacture of the aforementioned contrast medium for X-ray radiography; a method for X-ray radiography, which comprises the steps of administering liposomes containing any one of the aforementioned compounds as a membrane component to a mammal including human and then irradiating the mammal with an X-ray; and a method for radiography of a lesion of a vascular disease, which comprises the steps of administering liposomes containing any one of the aforementioned compounds as a membrane component to a mammal including human and then irradiating the mammal with an X-ray.

The present invention further provides a liposome, which contains any of the aforementioned compounds or a salt thereof at least one of which iodine atoms is a radioisotope as a membrane component, and a contrast medium for scintigraphy, which comprises the aforementioned liposome. As preferred embodiments of the invention, provided are the aforementioned contrast medium for scintigraphy, which is used for scintigraphy of vascular smooth muscle cells which are abnormally proliferated under an influence of foam macrophages; the aforementioned contrast medium for scintigraphy, which is used for scintigraphy of a tissue or lesion where macrophages localize; the aforementioned contrast medium for scintigraphy, wherein the tissue as the object of scintigraphy is selected from the group consisting of blood vessel, liver, spleen, air vesicle, lymph node, lymph vessel, and renal epithelium; and the aforementioned contrast medium for scintigraphy, which is used for scintigraphy of a lesion selected from the group consisting of lesions of tumor, arteriosclerosis, inflammation, and infection.

The present invention further provides use of any one of the aforementioned compounds or a salt thereof for manufacture of the aforementioned contrast medium for scintigraphy; a method for scintigraphy, which comprises the steps of administering liposomes containing any one of the aforementioned compounds as a membrane component to a mammal including human and then detecting radioactivity emitted by the liposomes; and a method for scintigraphy of a lesion of vascular disease, which comprises the steps of administering liposomes containing any one of the aforementioned compounds as a membrane component to a mammal including human and then detecting radioactivity emitted by the liposomes.

BEST MODE FOR CARRYING OUT THE INVENTION

Figure 1:
FIG. 1 is a radiographic photograph of a rat immediately before administration of liposomes of the present invention.

When a functional group is referred to as "substituted or unsubstituted" or "may be substituted" in the specification, the functional group is meant to have one or more substituents. Unless otherwise specifically mentioned, number, substituting position, and type of a substituent to be bound are not particularly limited. When a functional group has two or more substituents, they may be the same or different. In the specification, when a functional group has a substituent, example of the substituent include a halogen atom (the "halogen atom" herein referred to may be any of fluorine, chlorine, bromine, and iodine), an alkyl group (the "alkyl group" herein referred to may be any of straight, branched, cyclic, and a combination thereof, and the cyclic alkyl group include a polycyclic alkyl group such as a bicycloalkyl group. Alkyl moieties of other substituents containing the alkyl moieties have the same meaning), an alkenyl group (including a cycloalkenyl group and a bicycloalkenyl group), an alkynyl group, an aryl group, a heterocyclic group, cyano group, hydroxyl group, nitro group, carboxyl group, an alkoxyl group, an aryloxy group, a silyloxy group, a heterocyclyloxy group, an acyloxy group, a carbamoyloxy group, an alkoxycarbonyloxy group, an aryloxycarbonyloxy group, an amino group (including an anilino group), an acylamino group, an aminocarbonylamino group, an alkoxycarbonylamino group, an aryloxycarbonylamino group, a sulfamoylamino group, an alkyl or arylsulfonylamino group, a mercapto group, an alkylthio group, an arylthio group, a heterocyclylthio group, a sulfamoyl group, sulfo group, an alkyl or arylsulfinyl group, an alkyl or arylsulfonyl group, an acyl group, an aryloxycarbonyl group, an alkoxycarbonyl group, a carbamoyl group, an aryl or heterocyclylazo group, an imido group, a phosphino group, a phosphinyl group, a phosphinyloxy group, a phosphinylamino group, and a silyl group.

In the specification, $Ar^1$ represents hydrogen atom or an aryl group substituted with at least one iodine atom. $Ar^2$ represents an aryl group substituted with at least one iodine atom. It is more preferred that $Ar^1$ and $Ar^2$ independently represent an aryl group substituted with at least one iodine atom. The number of the iodine atoms that substitute on the ring of the aryl group is not particularly limited so long as the number is 1 or more. The number is most preferably 3 or more. The type of the aryl group is not particularly limited. Anthracenyl group, naphthalenyl group, and phenyl group are preferred, and phenyl group is most preferred (the other aryl groups herein referred to have the same meaning). The positions of the iodine atoms present on the ring of the aryl group represented by $Ar^1$ or $Ar^2$ are not particularly limited, and the atoms may present at any positions on the ring. The aryl group may have one or more substituents other than iodine atom. When the aryl group has one or more substituents other than the iodine atom(s), the type, number and substituting position of the substituent are not particularly limited. Preferred examples of the substituent on the aryl group include a halogen atom, an alkyl group, cyano group, hydroxyl group, an alkoxyl group, an amino group, an acylamino group, an acyl group, carboxyl group, an alkoxycarbonyl group and a carbamoyl group. Further, it is also preferred that the aryl group does not have any substituent other than the iodine atom(s).

When $Ar^1$ and $Ar^2$ each represent a triiodophenyl group, the substituting positions of three of the iodine atoms on the aromatic ring are not particularly limited. Substitutions at "2,4,6-positions", "2,3,5-positions" and "3,4,5-positions" are preferred, substitution at "2,4,6-positions" and "2,3,5-positions" are more preferred, and substitution at "2,4,6-positions" is most preferred. The triiodophenyl group may be further substituted. When the triiodophenyl group has a substituent, preferred examples of the substituent are the same as those mentioned as examples of the substituents of the aryl group represented by $Ar^1$ or $Ar^2$. Further, it is also preferred that $Ar^1$ and $Ar^2$ do not have any substituent other than the three iodine atoms.

In the specification, $Ar^{11}$, $Ar^{12}$, $Ar^{13}$ and $Ar^{14}$ independently represents hydrogen atom or an aryl group substituted with at least one iodine atom, provided that $Ar^{11}$ and $Ar^{12}$ do not simultaneously represent hydrogen atom, and $Ar^{13}$ and $Ar^{14}$ do not simultaneously represent hydrogen atom. It is preferred that $Ar^{11}$, $Ar^{12}$, $Ar^{13}$ and $Ar^{14}$ independently represent an aryl group substituted with at least one iodine atom. The number of the iodine atoms substituting on the ring of the aryl group is not particularly limited so long as the number is 1 or more. The number is most preferably 3 or more. Type of the aryl group is not particularly limited. Anthracenyl group, naphthalenyl group, and phenyl group are preferred, and phenyl group is most preferred (the other aryl groups herein referred to have the same meaning). The positions of iodine atoms present on the ring of the aryl group represented by $Ar^{11}$, $Ar^{12}$, $Ar^{13}$ or $Ar^{14}$ are not particularly limited, and the atoms may present at any positions on the ring. The aryl group may have one or more substituents other than the iodine atom(s). When the aryl group has one or more substituent other than the iodine atom(s), the type, number, and substituting position of the substituent are not particularly limited. Preferred examples of the substituent of the aryl group include a halogen atom, an alkyl group, cyano group, hydroxyl group, an alkoxyl group, an amino group, an acylamino group, an acyl group, carboxyl group, an alkoxycarbonyl group, and a carbamoyl group. Further, it is also preferred that the aryl group does not have any substituent other than the iodine atom(s).

When $Ar^{11}$, $Ar^{12}$, $Ar^{13}$ and $Ar^{14}$ each represent a triiodophenyl group, the substituting positions of three of the iodine atoms on the aromatic ring are not particularly defined. Substitutions at "2,4,6-positions", "2,3,5-positions" and "3,4,5-positions" are preferred, substitution at "2,4,6-positions" and "2,3,5-positions" are more preferred, and substitution at "2,4,6-positions" is most preferred. The triiodophenyl group may be further substituted. When the triiodophenyl group has a substituent, preferred examples of the substituent are the same as those mentioned as examples of the substituents of the aryl group. Further, it is also preferred that the triiodophenyl group does not have any substituent other than the three iodine atoms.

$L^1$ and $L^2$ independently represent a divalent bridging group of which main chain contains six or more carbon atoms. In the specification, the "main chain" of the divalent bridging group means an atomic group in the bridging group consisting of two atoms in the bridging group, each of which is involved in the bonding with other functional group or atom to be bridged, and an atomic group connecting said two atoms with a minimum number of atoms. More specifically, the main chain of $L^1$ consists of two atoms in $L^1$, which are involved in the bondings with the carbonyl carbon and $Ar^1$, and an atomic group in $L^1$ connecting the aforementioned two atoms with a minimum number of atoms. The main chain of $L^2$ is the same as the main chain of $L^1$. Further, the main chain of $L^3$ consists of two atoms in $L^3$, which are involved in the bondings with the carbon atom in the 2-position of the glycerol and X, and an atomic group in $L^3$ connecting the aforementioned two atoms with a minimum number of atoms.

The divalent bridging group represented by $L^1$ or $L^2$ may be a saturated group, or may contain one or more unsaturated bonds. Further, said group may contain one or more heteroatoms (the "heteroatom" herein referred to means an any atom other than carbon atom such as nitrogen atom, oxygen atom and sulfur atom) in the main chain. The number of the heteroatoms in the main chain is not particularly defined. The number may preferably be 5 or less, more preferably 3 or less, and most preferably 1 or less. The positions of the heteroatoms in the main chain are also not particularly defined. When the number of the heteroatom is 1, the heteroatom preferably locates within the range of 5 atoms from the group of Ar.

The divalent bridging group represented by $L^1$ or $L^2$ may contain a functional group containing a heteroatom as a partial structure of the main chain. Examples of the functional group containing an unsaturated moiety or a heteroatom as a partial structure of the main chain of the divalent bridging group represented by $L^1$ or $L^2$ include, for example, an alkenyl group, an alkynyl group, an ester group (including carboxylic acid ester, carbonic acid ester, sulfonic acid ester and sulfinic acid ester), an amido group (including carbonamido, urethane, sulfonamido and sulfinamido), an ether group, a thioether group, a disulfide group, an amino group, an imido group and the like. The aforementioned functional groups may be further substituted. Two or more of these functional groups may exist in the main chain of $L^1$ or $L^2$, and positions of the groups are also not particularly limited. When two or more of the aforementioned functional groups exist in the main chain of $L^1$ or $L^2$, they may be the same or different.

Preferred examples of the partial structure included in the main chain of the divalent bridging group represented by $L^1$ or $L^2$ include an alkenyl group, an ester group, an amido group, an ether group, a thioether group, a disulfide group and an amino group, and more preferred are an alkenyl group, an ester group and an ether group. Further, it is also preferred that any heteroatom is not contained in the main chain and/or a functional group as a partial structure of the main chain. When a heteroatom is contained, the heteroatom is preferably oxygen atom or sulfur atom, and oxygen atom is most preferred. The carbon number of $L^1$ and $L^2$ is preferably 6 to 30, more preferably 6 to 25, most preferably 6 to 15. On the main chain of $L^1$ or $L^2$, one or more substituents may exist. When a substituent exists on the main chain of $L^1$ or $L^2$, the type, number and substituting position of the substituent are not particularly limited. Preferred examples of the substituent are, for example, a halogen atom, an alkyl group, hydroxyl group, oxo group and the like. Further, it is also preferred that any substituent does not exist on the main chains of $L^1$ or $L^2$.

Preferred embodiments of $L^1$ and $L^2$ are specifically exemplified below. However, the compounds of the present invention are not limited to those having these bridging groups. Each of the following exemplary groups binds to Ar at the right end.

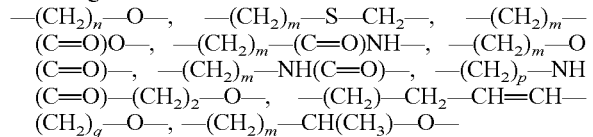

In the formula, n represents an integer of from 6 to 30; m represents an integer of from 5 to 29; p represents an integer of from 4 to 28; and q represents an integer of from 3 to 27.

$L^3$ represents a single bond or a divalent bridging group of which main chain consists of 1 to 6 carbon atoms and one oxygen atom. This bridging group may be a saturated group, or may contain an unsaturated bond. The oxygen atom contained in the main chain does not directly bind to X. Except for the above requirement, the position of the oxygen atom is not particularly defined. It is preferred that the oxygen atom directly binds to the carbon at the 2-position of the grycelol partial structure. The bridging group may further contain one or more heteroatoms in the main chain. In such a group, the heteroatoms are preferably selected from oxygen atom, nitrogen atom and sulfur atom (when one or more oxygen atoms are contained as the aforementioned heteroatoms, $L^3$ is a divalent bridging group of which main chain contains 1 to 6 carbon atoms and one oxygen atom and further contains one or more oxygen atoms). The number of the heteroatoms contained in the main chain is not particularly limited, and the number is preferably 3 or less, more preferably 1, in total. The number of carbon atom in $L^3$ is preferably 1 to 4. The main chain of $L^3$ may be substituted. In such a group, type, number, and substituting position of the substituent are not particularly limited. The substituent is preferably selected from an alkyl group, an alkoxyl group, hydroxyl group, amino group, carboxyl group and the like. Further, for example, any carbon atom constituting $L^3$ may bind to an oxygen atom to form carbonyl group. It is also preferred that no substituent exists on the main chain of $L^3$, and $L^3$ also preferably represents a single bond.

Preferred specific examples of $L^3$ are shown below. However, the compound of the present invention is not limited to those having the following bridging groups. As for the following examples, each of the groups binds to the group X at the left end.

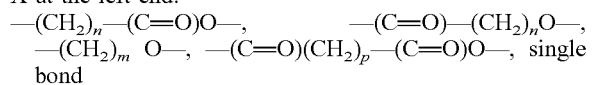

In the formulas, n represents an integer of 0 to 5; m represents an integer of 1 to 6; and p represents an integer of 1 to 4.

$L^{11}$, $L^{12}$, $L^{13}$ and $L^{14}$ independently represent a divalent bridging group of which main chain contains 6 or more carbon atoms. The "main chain" has the meaning defined above. More specifically, the main chain of $L^{11}$ consists of two atoms in $L^{11}$, which are involved in the bindings with the carbonyl carbon and $Ar^{11}$, and an atomic group connecting said two atoms with a minimum number of atoms. The main chains of $L^{12}$, $L^{13}$ and $L^{14}$ have the same meaning as the main chain of $L^{11}$.

The divalent bridging group represented by $L^{11}$, $L^{12}$, $L^{13}$ or $L^{14}$ may be a saturated group, or may contain one or more unsaturated bonds. Further, said group may contain one or more heteroatoms in the main chain. The number of the heteroatoms in the main chain is not particularly defined, and the number is preferably 5 or less, more preferably 3 or less, and most preferably 1 or less. The positions of the heteroatoms in the main chain are also not particularly limited. When the number of the heteroatom is 1, the heteroatom preferably locates within the range of 5 atoms from the group of Ar.

The divalent bridging group represented by $L^{11}$, $L^{12}$, $L^{13}$ or $L^{14}$ may contain a functional group containing a heteroatom as a partial structure of the main chain. Examples of the functional group containing an unsaturated moiety or a heteroatom as a partial structure of the main chain of the divalent bridging group represented by $L^{11}$, $L^{12}$, $L^{13}$ or $L^{14}$ include, for example, an alkenyl group, an alkynyl group, an ester group (including carboxylic acid ester, carbonic acid ester, sulfonic acid ester and sulfinic acid ester), an amido group (including carbonamido, urethane, sulfonamido and sulfinamido), an ether group, a thioether group, a disulfide group, an amino group, an imido group and the like. The aforementioned functional groups may be further substituted. Two or more of these functional groups may exist in the main chains of $L^{11}$, $L^{12}$, $L^{13}$ or $L^{14}$, and positions of the groups are not also particularly limited. When two or more of the aforementioned functional groups exist in the main chains of $L^{11}$, $L^{12}$, $L^{13}$ or $L^{14}$, they may be the same or different.

Preferred examples of the partial structure included in the main chain of the divalent bridging group represented by $L^{11}$, $L^{12}$, $L^{13}$ or $L^{14}$ include an alkenyl group, an ester group, an amido group, an ether group, a thioether group, a disulfide group and an amino group, and more preferred are an alkenyl group, an ester group and an ether group. Further, it is also preferred that any heteroatom is not contained in the main chain and/or a functional group as a partial structure of the main chain. When a heteroatom is contained, the heteroatom is preferably oxygen atom or sulfur atom, and oxygen atom is most preferred. The carbon number of $L^{11}$, $L^{12}$, $L^{13}$ and $L^{14}$ is preferably 6 to 30, more preferably 6 to 25, most preferably 6 to 15. On the main chain of $L^{11}$, $L^{12}$, $L^{13}$ or $L^{14}$, one or more substituents may exist. When a substituent exists on the main chain of $L^{11}$, $L^{12}$, $L^{13}$ or $L^{14}$, type, number and substitution position of the substituent are not particularly limited. Preferred examples of the substituent are, for example, a halogen atom, an alkyl group, hydroxyl group, oxo group and the like. Further, it is also preferred that no substituent exists on the main chain of $L^{11}$, $L^{12}$, $L^{13}$ or $L^{14}$.

Preferred embodiments of $L^{11}$, $L^{12}$, $L^{13}$ and $L^{14}$ are specifically exemplified below. However, the compounds of the present invention are not limited to those having these bridging groups. In addition, each of the following exemplary groups binds to Ar at the right end.

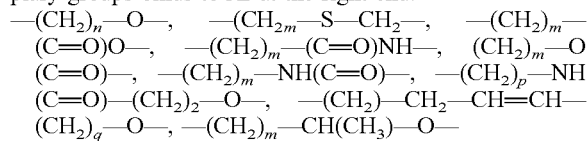

In the formula, n represents an integer of 6 to 30; m represents an integer of 5 to 29; p represents an integer of 4 to 28; and q represents an integer of 3 to 27.

X represents a functional group containing at least one heteroatom. Type of the heteroatom is not particularly limited. The heteroatom is preferably selected from the group consisting of nitrogen atom, oxygen atom and sulfur atom, and nitrogen atom or oxygen atom is more preferred. When two or more heteroatoms are included, they may be the same or different. The number of the heteroatom is also not particularly limited, and the number is preferably 30 or less, more preferably 20 or less, further preferably 12 or less. Examples of the functional group represented by X include, for example, an amino group (including a quaternary ammonium group), hydroxyl group, an alkoxyl group, an acylamino group, an aminocarbonyl group, carboxyl group, a sulfoxy group, a thiol group, a thioether group, an alkoxycarbonyl group, an aryloxycarbonyl group, an acyloxy group and the like, and an amino group (including a quaternary ammonium group), hydroxyl group, an alkoxyl group, carboxyl group and the like are more preferred. However, the functional group is not limited to these examples. Further, these functional groups may have one or more substituents, and in such a group, type and substitution position of the substituents are not particularly limited.

Further, a more preferred embodiment of X includes a group represented by $-N(R^1)(R^2)$. In the formula, $R^1$ and $R^2$ independently represent hydrogen atom, an alkyl group having 1 to 10 carbon atoms which may be substituted, or an acyl group having 1 to 10 carbon atoms which may be substituted. The acyl group may by any of an aliphatic acyl group such as an alkanoyl group or an aromatic acyl group such as an arylcarbonyl group. The carbon numbers of $R^1$ and $R^2$ are more preferably 1 to 5. $R^1$ and $R^2$ may bind to each other to form a ring. When a ring is formed, the ring may contain a substituent of $R^1$ or $R^2$ as ring-constituting atoms. Preferred example of X include, for example, amino group, methylamino group, dimethylamino group, acetylamino group, pyrrolidino group, piperidino group, piperazino group, morpholino group and the like. Among them, amino group, dimethylamino group, and morpholino group are more preferred, and morpholino group is most preferred. However, X is not limited to these groups.

Furthermore, it is also preferred that X is a group represented by $-O-R^3$. In the formula, $R^3$ represents hydrogen atom, an alkyl group having 1 to 10 carbon atoms which may be substituted, or an acyl group having 1 to 10 carbon atoms which may be substituted. The carbon numbers of the alkyl group and acyl group represented by $R^3$ are more preferably 1 to 6. When the alkyl group or acyl group represented by $R^3$ is substituted, type, number and substituting position of the substituents are not particularly limited. Preferred examples of the substituent include an acyl group, an amino group (including a quaternary ammonium group), hydroxyl group, an alkoxyl group, an acylamino group, an aminocarbonyl group, a ureido group, carboxyl group, a sulfoxy group, a thiol group, a thioether group, an alkoxycarbonyl group, an aryloxycarbonyl group, an acyloxy group and the like. However, the substituent is not limited to these examples. Further, the alkyl group or acyl group represented by $R^3$ may have two or more of these substituents, and these substituents may further have another substituent.

More preferably, the alkyl group or acyl group represented by $R^3$ has an alkoxyl group, hydroxyl group or an amino group (including a quaternary ammonium group) as a substituent. More specifically, preferred embodiments of R3 include, indicated as a form of $R^3OH$, ethylenediol, glycerin, inositol, glucose, galactose, serine, glutamic acid and the like, but not limited to these examples. Further, it is also preferred that $R^3$ is a group represented by $R^4(OCH_2CH_2)_n-$ (in the formula, $R^4$ represents hydrogen atom, methyl group, or ethyl group; and n represents an integer of 1 to 5). In the aforementioned group, n is preferably 1 to 3, and $R^4$ is preferably hydrogen atom or ethyl group.

$R^{11}$ and $R^{12}$ independently represent hydrogen atom or an alkyl group having two or more carbon atoms and having a functional group containing at least one or more heteroatoms as a substituent. The aforementioned alkyl group is constituted by preferably 2 to 20 carbon atoms, more preferably 2 to 10 carbon atoms. The type and number of the functional group containing at least one or more heteroatoms on the alkyl group is not particularly limited. The total carbon atom number is preferably 1 to 10, more preferably 1 to 6. When the alkyl group has two or more of the aforementioned functional groups, they may be same or different. The position of the aforementioned functional group existing on the alkyl group is not particularly limited.

The functional group containing at least one or more heteroatoms, which exists on the aforementioned alkyl group as a substituent, may be further substituted. Examples of the functional group containing at least one or more heteroatoms include an amino group (including a quaternary ammonium group), hydroxyl group, an alkoxyl group, an acylamino group, an aminocarbonyl group, carboxyl group, a sulfoxy group, a thiol group, a thioether group, an alkoxycarbonyl group, an aryloxycarbonyl group, an acyloxy group and the like, and an amino group (including a quaternary ammonium group), hydroxyl group, an alkoxyl group and carboxyl group are more preferred. However, the substituent is not limited to these examples. The heteroatom contained in the above functional group is preferably oxygen atom, nitrogen atom or sulfur atom, and oxygen atom and nitrogen atom are more preferred. More specifically, preferred embodiments of the alkyl group containing the functional group and represented by $R^{11}$ or $R^{12}$ include, indicated as a form of $R^{11}OH$ or $R^{12}OH$, for example, ethanolamine, serine, choline, glycerin, inositol, glucose, galactose, diethylene glycol and the like. However, the compound of the present invention is not limited to those having residues of these compounds.

The compounds of the present invention may have one or more asymmetric centers, and for such compounds, stereoisomers such as optically active substances and diastereoisomers based on the asymmetric centers may exist. Any of stereoisomers in pure forms, any mixtures of the stereoisomers, racemates thereof and the like all fall within the scope of the present invention. Further, the compounds of the present invention may have an olefinic double bond. The configuration may be either E-configuration or Z-configuration, or the compounds may be present as a mixture thereof. The compounds of the present invention may also exist as tautomers. Any tautomers or mixtures thereof fall within the scope of the present invention. Further, the compound of the present invention may form a salt depending on the type of a substituent, and the compound in a free form or the compound in a form of a salt may form a hydrate or a solvate. All of these substances also fall within the scope of the present invention. A type of the salt is not particularly limited, and the salt may be an acid addition salt or base addition salt.

Preferred examples of the compounds of the present invention are shown below. However, the compounds of the present invention are not limited to these examples.

(1A-1) 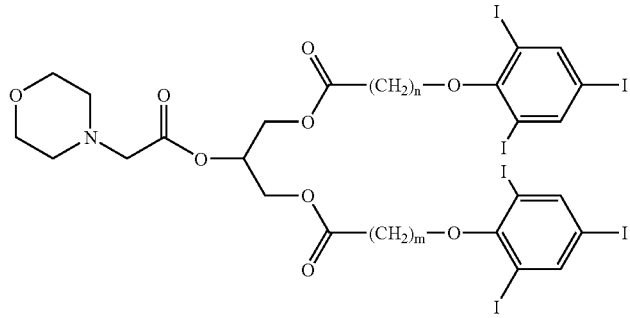

1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 10, m = 14

(1A-2) 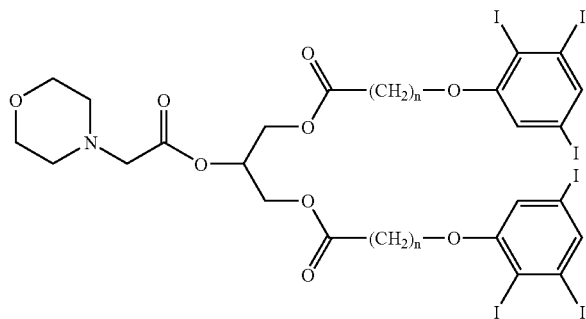

1: n = 6
2: n = 10
3: n = 12
4: n = 14
5: n = 16
6: n = 18
7: n = 20

(1A-3) 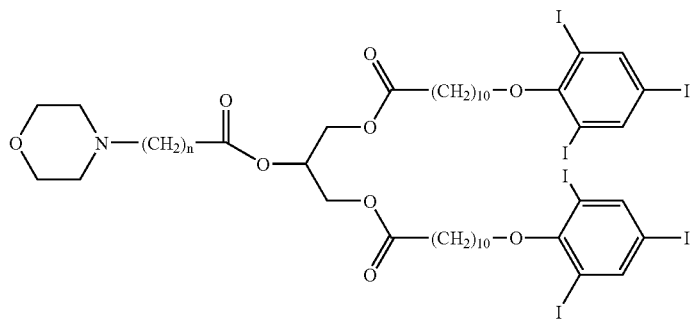

1: n = 2
2: n = 3
3: n = 4
4: n = 5

(1A-4) 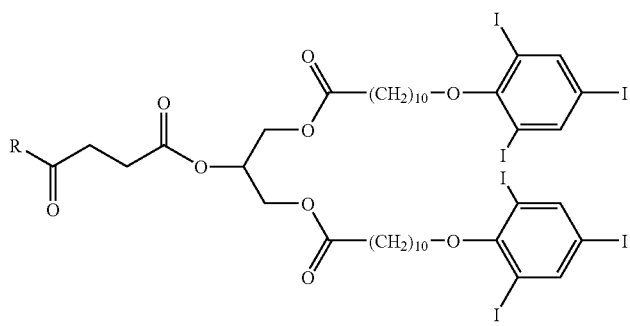

1: R = N⏋O (morpholino)
2: R = $NH_2$
3: R = $NMe_2$
4: R = OH
5: R = $Et(OCH_2CH_2)_3O$
6: R = $H(OCH_2CH_2)_3O$
7: R = $HOCH_2CH_2O$
8: R = –CH$_2$–CH(OH)–CH$_2$OH
9: R = –CH(CH$_2$OH)$_2$ -continued (1A-5)

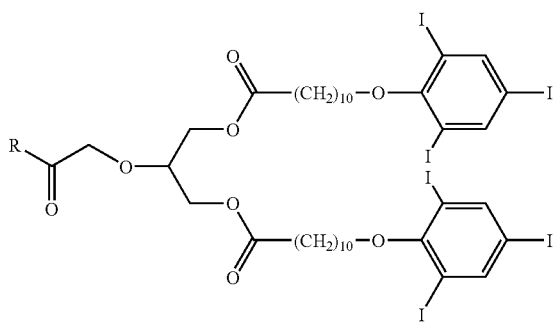

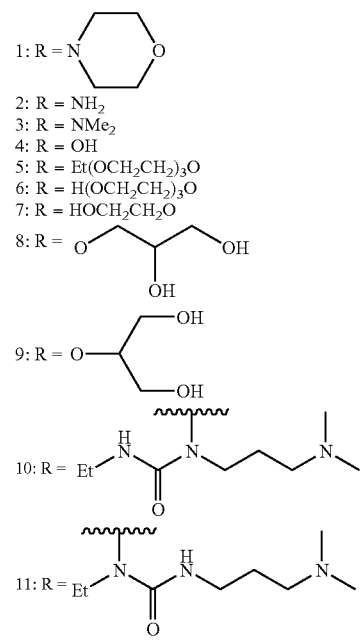

1: R = N-morpholine
2: R = NH$_2$
3: R = NMe$_2$
4: R = OH
5: R = Et(OCH$_2$CH$_2$)$_3$O
6: R = H(OCH$_2$CH$_2$)$_3$O
7: R = HOCH$_2$CH$_2$O
8: R = OCH$_2$CH(OH)CH$_2$OH
9: R = OCH(CH$_2$OH)$_2$
10: R = Et-NH-C(O)-N(CH$_2$CH$_2$CH$_2$NMe$_2$)-
11: R = Et-N(C(O)NH-CH$_2$CH$_2$CH$_2$NMe$_2$)-

(1A-6)

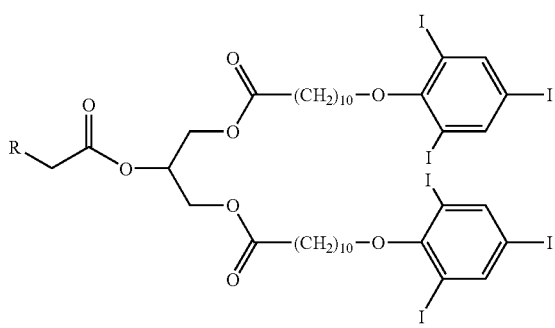

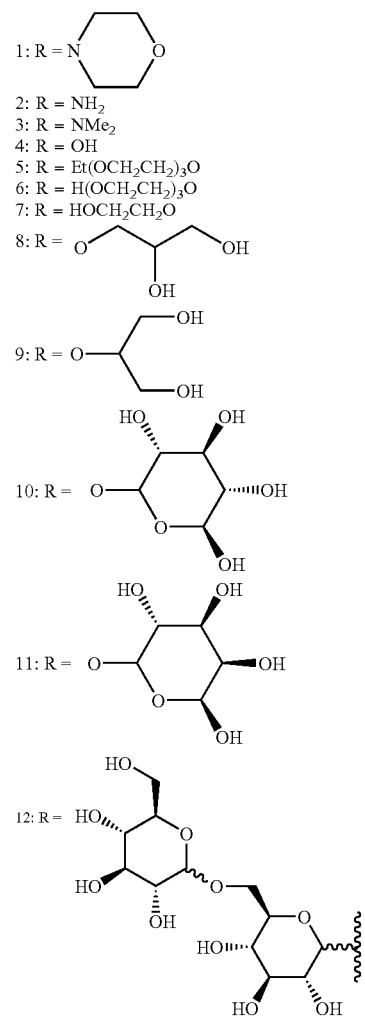

1: R = N-morpholine
2: R = NH$_2$
3: R = NMe$_2$
4: R = OH
5: R = Et(OCH$_2$CH$_2$)$_3$O
6: R = H(OCH$_2$CH$_2$)$_3$O
7: R = HOCH$_2$CH$_2$O
8: R = OCH$_2$CH(OH)CH$_2$OH
9: R = OCH(CH$_2$OH)$_2$
10: R = glucopyranosyl-O-
11: R = glucopyranosyl-O-
12: R = disaccharide (1A-7) 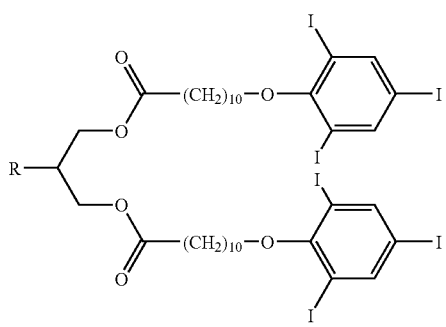
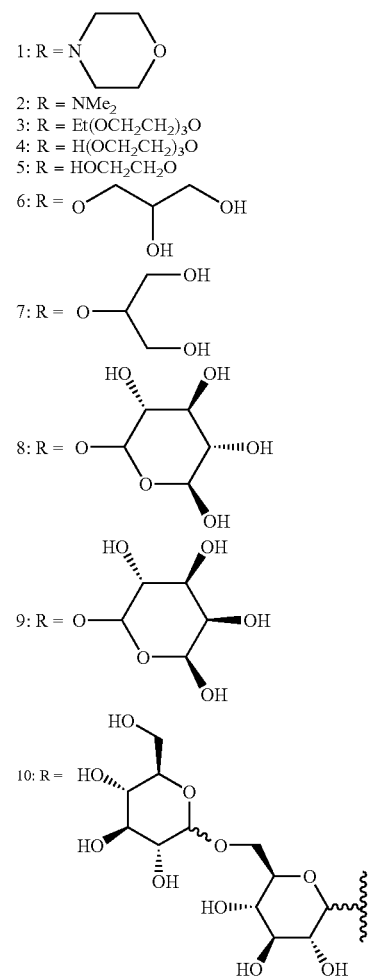
1: R = N-morpholino
2: R = NMe$_2$
3: R = Et(OCH$_2$CH$_2$)$_3$O
4: R = H(OCH$_2$CH$_2$)$_3$O
5: R = HOCH$_2$CH$_2$O
6: R = (glycerol-1-yl)
7: R = (glycerol-2-yl)
8: R = (hexopyranosyl)
9: R = (hexopyranosyl)
10: R = (disaccharide)
(1A-8) 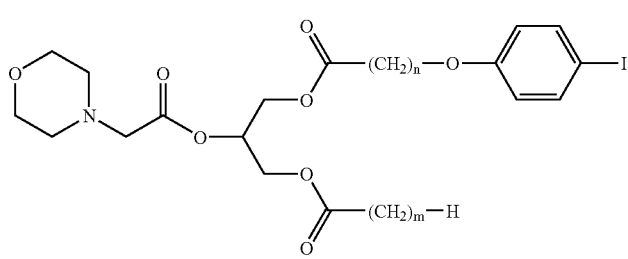
1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 10, m = 14
(1A-9) 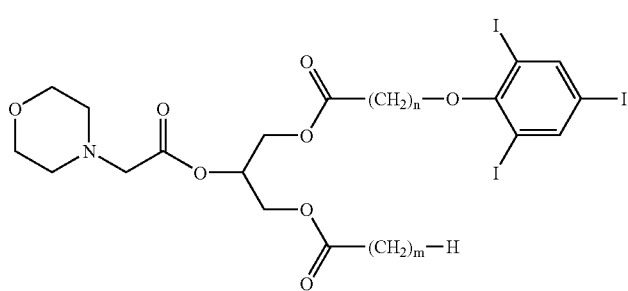
1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 10, m = 14

(1B-1)
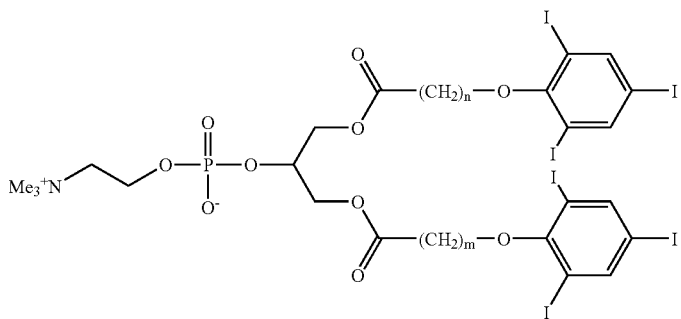
1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 10, m = 14
(1B-2)
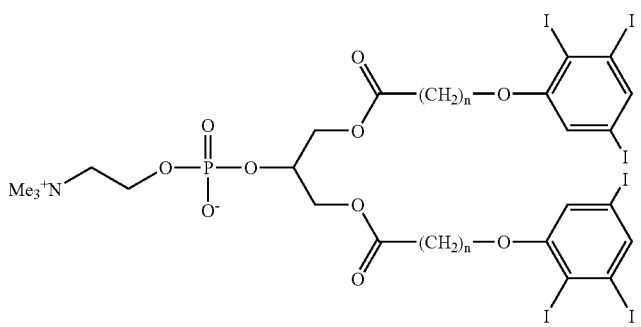
1: n = 6
2: n = 10
3: n = 12
4: n = 14
5: n = 16
6: n = 18
7: n = 20
(1B-3)
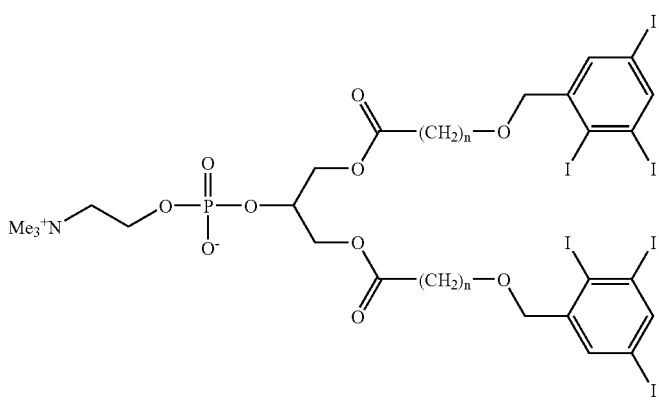
1: n = 5
2: n = 9
3: n = 11
4: n = 13
5: n = 15
6: n = 17
7: n = 19
(1B-4)
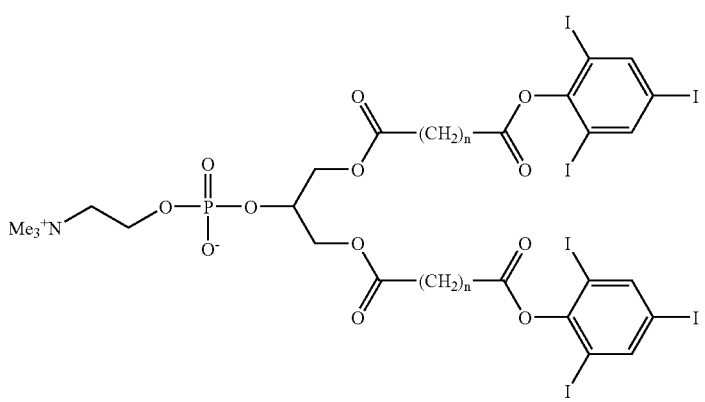
1: n = 5
2: n = 9
3: n = 11
4: n = 13
5: n = 14
6: n = 15
7: n = 17
8: n = 19

(1B-5)
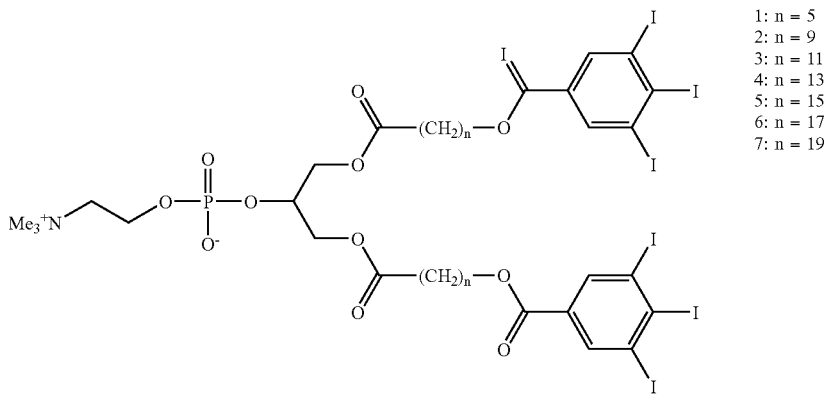
1: n = 5
2: n = 9
3: n = 11
4: n = 13
5: n = 15
6: n = 17
7: n = 19
(1B-6)
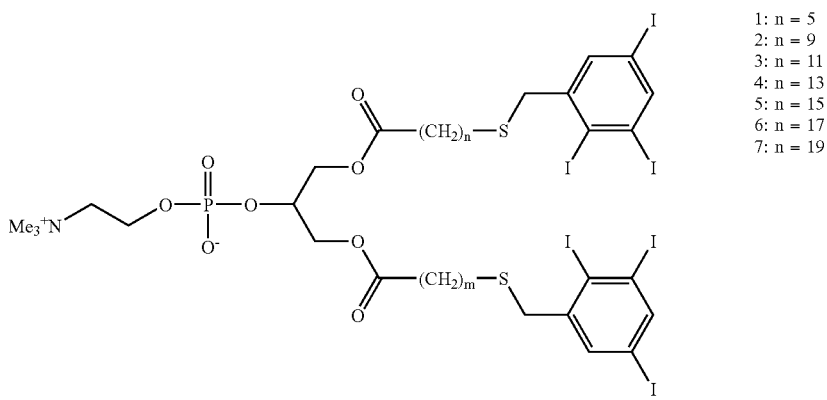
1: n = 5
2: n = 9
3: n = 11
4: n = 13
5: n = 15
6: n = 17
7: n = 19
(1B-7)
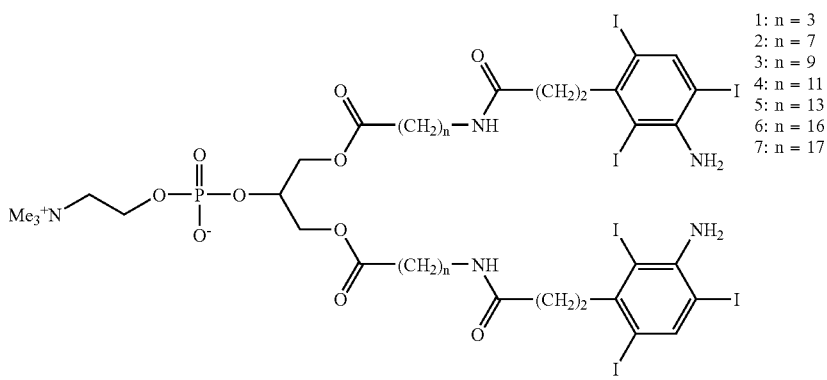
1: n = 3
2: n = 7
3: n = 9
4: n = 11
5: n = 13
6: n = 16
7: n = 17
(1B-8)
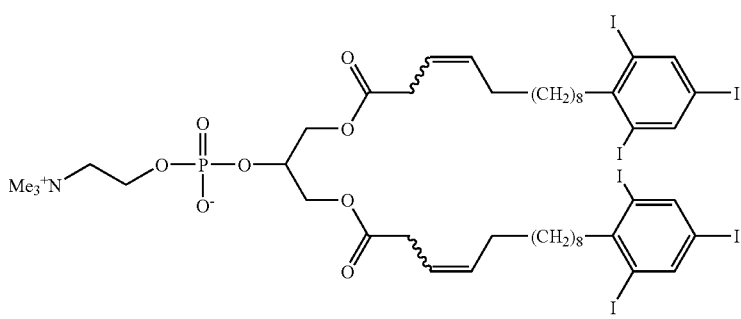

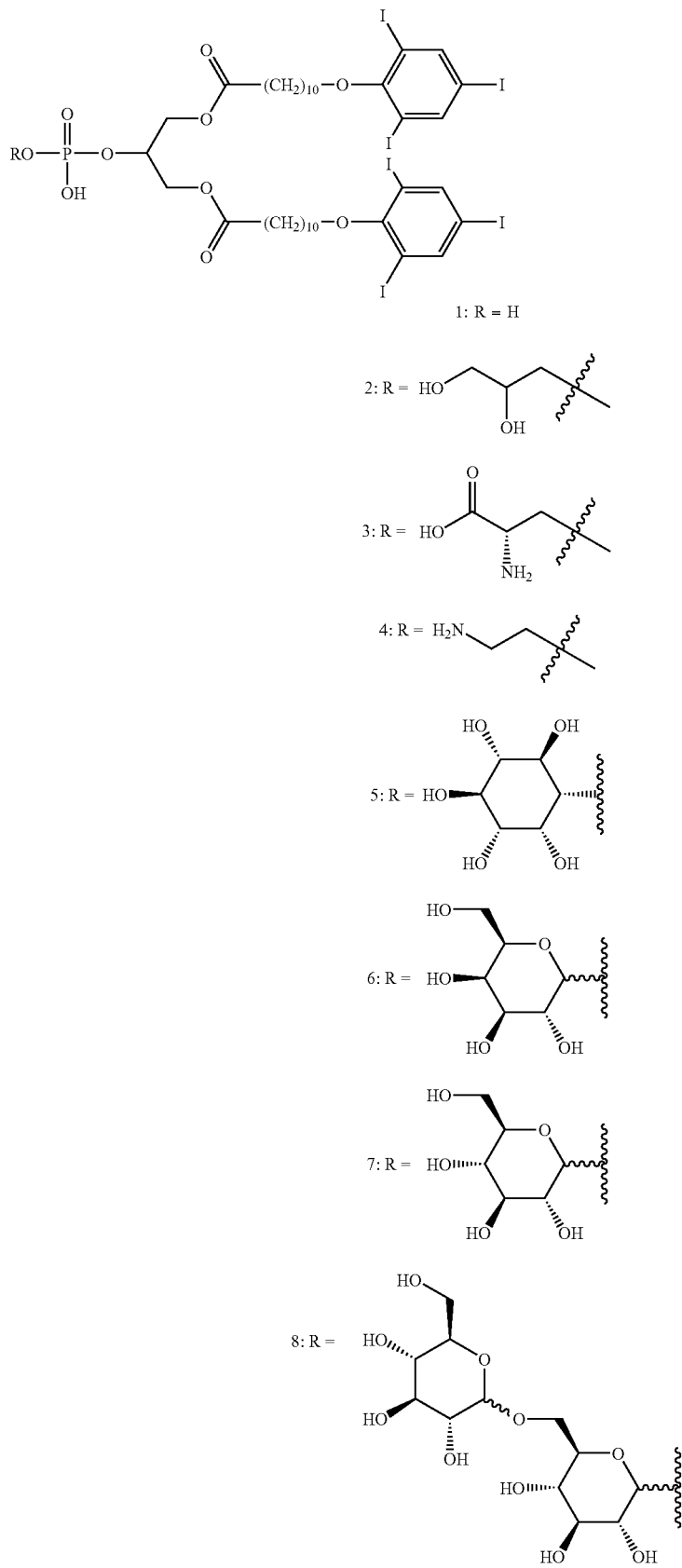

-continued
(1B-10)
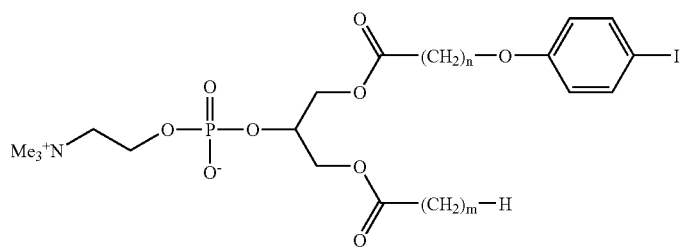
1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 10, m = 14
(1B-11)
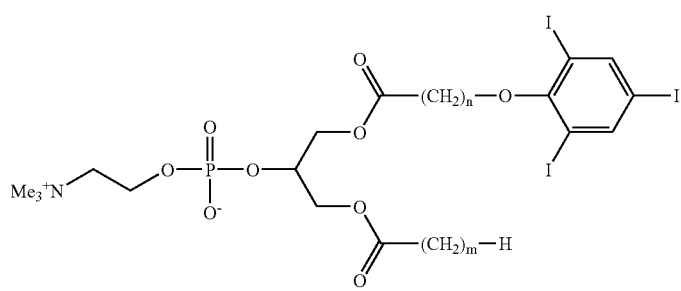
1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 10, m = 14
(2B-1)
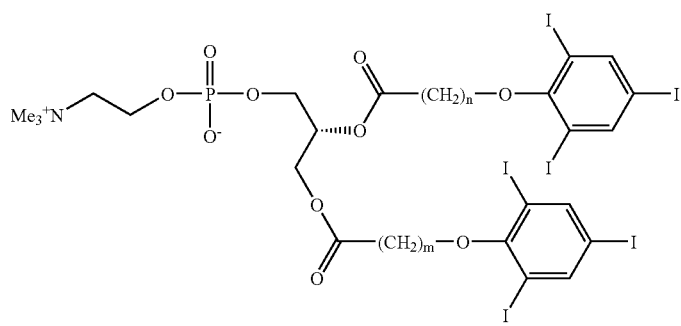
1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 14, m = 10
16: n = 10, m = 14
(2B-2)
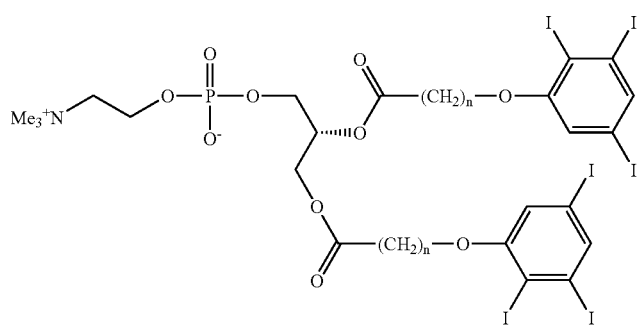
1: n = 6
2: n = 10
3: n = 12
4: n = 14
5: n = 16
6: n = 18
7: n = 20

-continued
(2B-3) 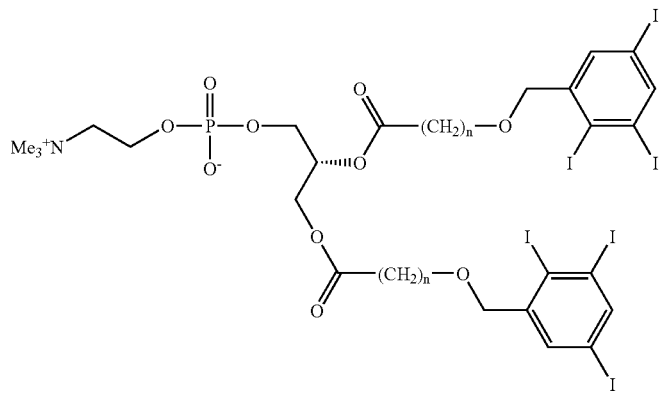
1: n = 5
2: n = 9
3: n = 11
4: n = 13
5: n = 15
6: n = 17
7: n = 19
(2B-4) 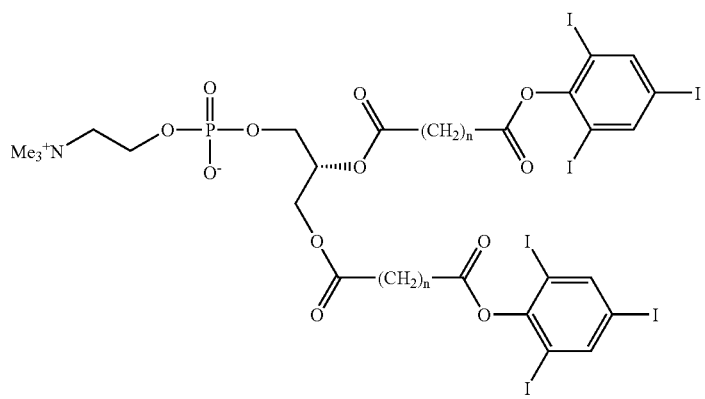
1: n = 5
2: n = 9
3: n = 11
4: n = 13
5: n = 14
6: n = 15
7: n = 17
8: n = 19
(2B-5) 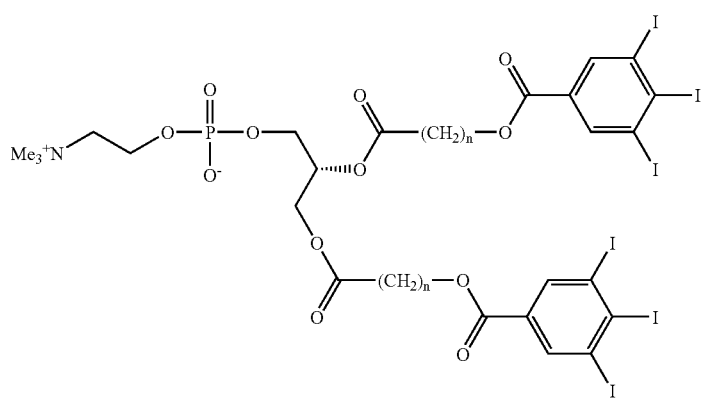
1: n = 5
2: n = 9
3: n = 11
4: n = 13
5: n = 15
6: n = 17
7: n = 19
(2B-6) 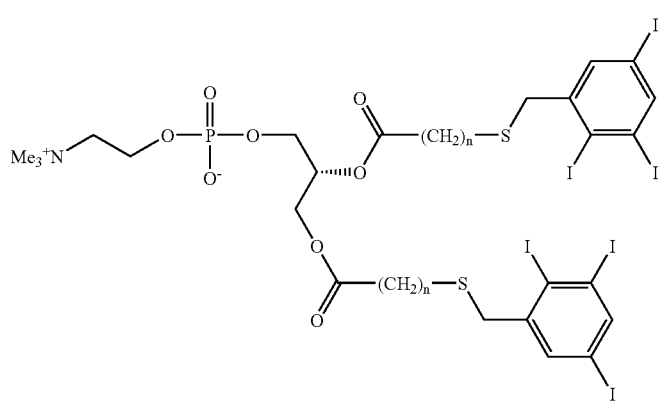
1: n = 5
2: n = 9
3: n = 11
4: n = 13
5: n = 15
6: n = 17
7: n = 19

-continued
(2B-7)
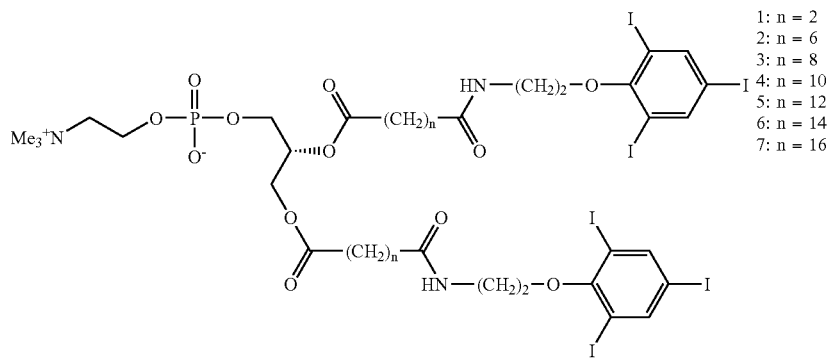
1: n = 2
2: n = 6
3: n = 8
4: n = 10
5: n = 12
6: n = 14
7: n = 16
(2B-8)
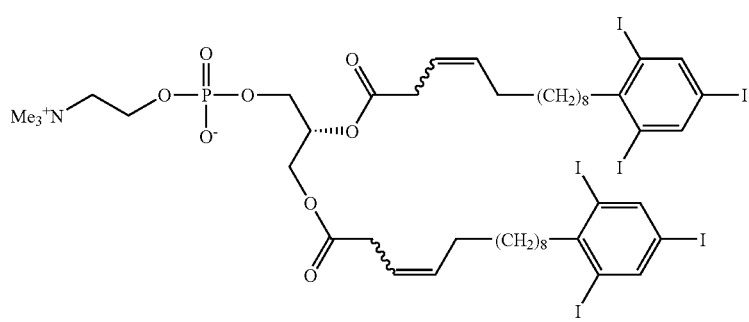
(2B-9)
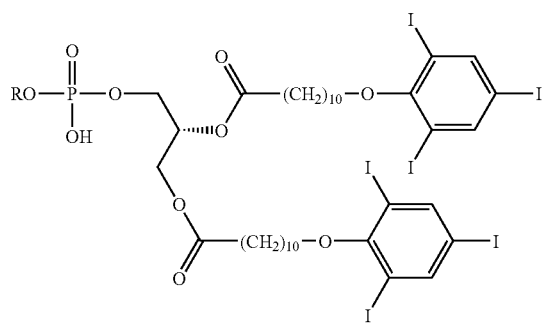
1: R = H
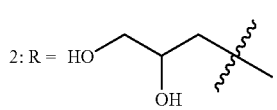
2: R =
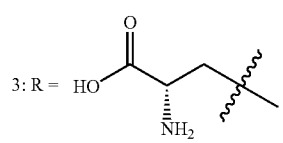
3: R =
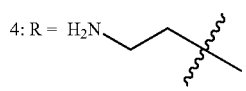
4: R =
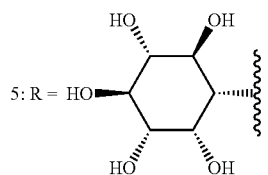
5: R =

-continued
6: R = 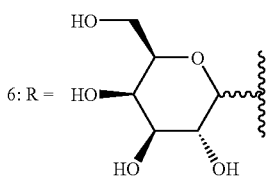
7: R = 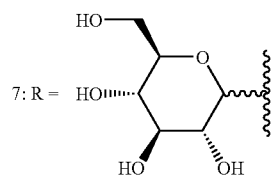
8: R = 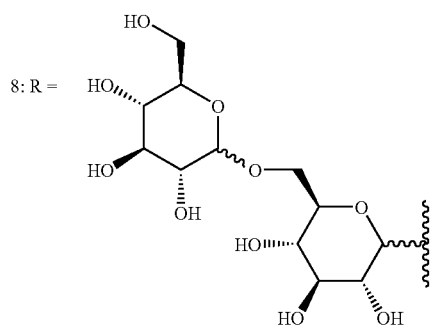
(2B-10) 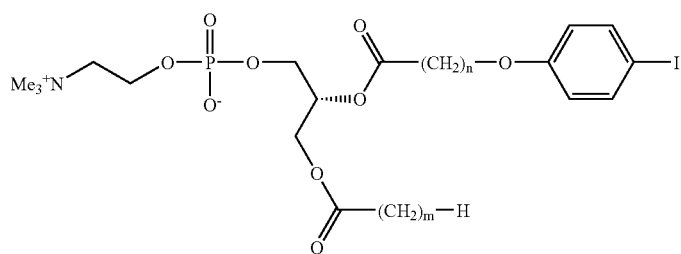
1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 14, m = 10
16: n = 10, m = 14
(2B-11) 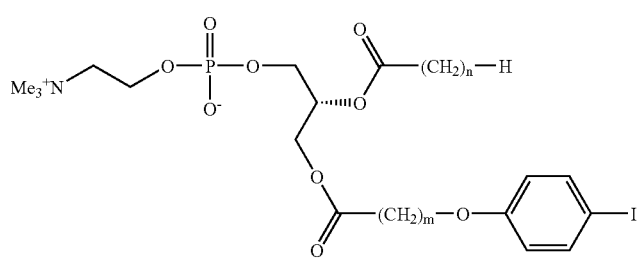
1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 14, m = 10
16: n = 10, m = 14

(2B-12)

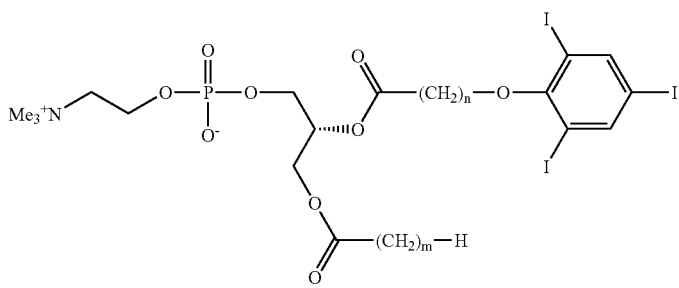

1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 14, m = 10
16: n = 10, m = 14

(2B-13)

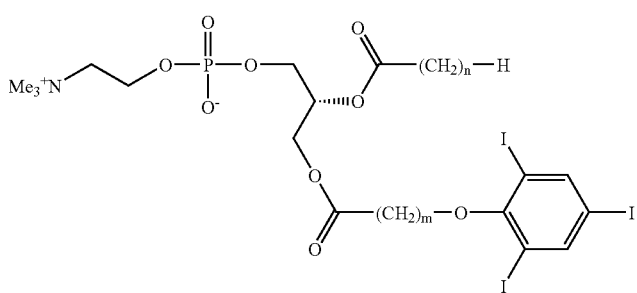

1: n = m = 6
2: n = m = 8
3: n = m = 10
4: n = m = 11
5: n = m = 12
6: n = m = 13
7: n = m = 14
8: n = m = 15
9: n = m = 16
10: n = m = 17
11: n = m = 18
12: n = m = 20
13: n = m = 25
14: n = m = 30
15: n = 14, m = 10
16: n = 10, m = 14

Synthetic methods for the compounds of the present invention, in general, will be explained below. However, synthetic methods of the compounds of the present invention are not limited to these methods. As starting materials for preparation which have an iodoaryl group, especially triiodophenyl group, used for the compounds of the present invention, those ordinarily commercially available may be used, or they may be suitably synthesized depending on purposes. As commercially available products, for example, 2,4,6-triiodophenol and benzoic acid derivatives (for example, 3-amino-2,4,6-triiodobenzoicacid, acetrizoic acid, iopipamide, diatrizoic acid, histodenz, 5-amino-2,4,6-triiodoisophthalic acid, 2,3,5-triiodobenzoic acid, tetraiodo-2-sulfobenzoic acid), iopanoic acid, iophenoxic acid and the like can be used. When the compounds are obtained by syntheses, iodine atoms can be introduced on an aromatic ring by, for example, the method described by Richard C. Larock in Comprehensive Organic Transformations (VCH) for use as raw materials.

Since the aforementioned triiodophenyl derivatives usually have a functional group such as hydroxyl group, amino group, thiol group, and carboxyl group as a partial structure, these functional groups can also be condensed with a dibasic carboxylic acid, halogenated aliphatic acid, hydroxy aliphatic acid or the like via an ether bond, ester bond, amino bond, amide bond or the like to prepare a carboxylic acid having a triiodophenyl group, and the resulting compound can be used as synthetic intermediates for the compounds of the present invention. In these steps, a protective group may also be used, if necessary. As the protective group, those described by T. W. Green & P. G. M. Wuts in Protecting Groups in Organic Synthesis (John Wiley & Sons, Inc.) can be used, for example. Examples of the dibasic carboxylic acid include, for example, dodecanedioic acid, tetradecanedioic acid, docosanedioic acid, 4,4'-dithiobutanedioic acid and the like. Examples of the halogenated aliphatic acid include, for example, 12-bromododecanoic acid and 16-bromohexadecanoic acid. Examples of the hydroxy aliphatic acid include, for example, 10-hydroxydecanoic acid, 12-hydroxydodecanoic acid, 12-hydroxystearic acid and the like. However, these compounds are given as examples, and the dibasic carboxylic acids are not limited to these examples.

The compounds of the present invention may have an alkyl group with any length, and if no suitable synthetic raw material is available, the raw material can be appropriately obtained by synthesis. Examples of the synthetic methods include, for example, Wittig reaction, Barbier-Wieland degradation, Arndt-Eistert synthesis, a method using acetylide (according to, for example, the method described in Tetrahedron Lett., 35, 9501 (1994)), a method using a chloroformic acid ester (described in, for example, Synthesis, 427 (1986)), a method using diethyl malonate (described in, for example, Arch. Pharm. (Weinheim) 328, 271 (1995)) and the like. However, the above methods are given as examples, and the synthetic methods are not limited to these examples.

Diacylglycerol compounds as precursors of the compounds of the present invention can be synthesized by derivatization, for example, according to the method described in J. Med. Chem., 29 (12), 2457 (1986) by using these carboxylic acids having a triiodophenyl group as raw material compounds. Moreover, similar diacylglycerol compounds can also be synthesized by, for example, subjecting a glycerin derivative such as glyceraldehyde and 2,2-dimethyl-1,3-dioxolane-4-methanol stepwise to esterification, deprotection/reduction and esterification. The compounds of the present invention in the form of phosphoric acid esters can be synthesized by derivatization of these diacylglycerol compounds, for example, according to the methods described in J. Org. Chem., 64, 7727 (1999); J. Org. Chem., 64, 648 (1999) and the like.

The compounds of the present invention and salts thereof can be used as membrane components of liposomes. When liposomes are prepared by using the compounds of the present invention or salts thereof, a content of the compounds of the present invention and salts thereof in the liposomes is about from 10 to 90 mass %, preferably from 10 to 80 mass %, more preferably from 20 to 80 mass %, based on the total mass of the membrane components of the liposome. One kind of the compound of the present invention or salt thereof may be used as a membrane component, or two or more kinds of the compounds of the present invention and salts thereof may be used in combination.

As other membrane components constituting the liposome, any of lipid compounds ordinarily used for preparation of liposomes can be used. For example, such compounds are described in Biochim. Biophys. Acta, 150 (4), 44 (1982); Adv. in Lipid. Res., 16 (1) 1 (1978); "RESEARCH IN LIPOSOMES", P. Machy, L. Leserman, John Libbey EUROTEXT Co.; "Liposome" (Ed., Nojima, Sunamoto and Inoue, Nankodo) and the like. As the lipid compounds, phospholipids are preferred, and phosphatidylcholines (PC) are particularly preferred. Preferred examples of phosphatidylcholines include, but not limited thereto, egg PC, dimyristoyl-PC (DMPC), dipalmitoyl-PC (DPPC), distearoyl-PC (DSPC), dioleyl-PC (DOPC) and the like.

According to a preferred embodiment of the present invention, a phosphatidylcholines and a phosphatidylserine (PS) can be used in combination. Examples of the phosphatidylserine include those having lipid moieties similar to those of the phospholipids mentioned as preferred examples of the phosphatidylcholine. When a phosphatidylcholine and a phosphatidylserine are used in combination, molar ratio of PC and PS (PC:PS) used is preferably in the range of 90:10 to 10:90, further preferably 30:70 to 70:30.

Another preferred embodiment of the liposome of the present invention includes a liposome containing a phosphatidylcholine and a phosphatidylserine and further containing a phosphoric acid dialkyl ester as membrane components. The two alkyl groups constituting the dialkyl ester of phosphoric acid are preferably the same groups. Each group may contain 6 or more carbon atoms, preferably 10 or more carbon atoms, more preferably 12 or more carbon atoms. Preferred examples of the phosphoric acid dialkyl ester include, but not limited thereto, dilauryl phosphate, dimyristyl phosphate, dicetyl phosphate and the like. In this embodiment, preferred amount of the phosphoric acid dialkyl ester is from 1 to 50 mass %, preferably from 1 to 30 mass %, further preferably from 1 to 20 mass %, based on the total mass of phosphatidylcholine and phosphatidylserine.

In the liposome containing a phosphatidylcholine, a phosphatidylserine, a phosphoric acid dialkyl ester and the compound of the present invention as membrane components, preferred weight ratio of PC, PS, phosphoric acid dialkyl ester and the compound of the present invention may be chosen from 5 to 40 mass %: from 5 to 40 mass %: from 1 to 10 mass %: from 15 to 80 mass %.

The components of the liposome of the present invention are not limited to the aforementioned four kinds of compounds, and other components may be added. Examples of such components include cholesterol, cholesterol esters, sphingomyelin, monosial ganglioside GM1 derivatives described in FEBS Lett., 223, 42 (1987); Proc. Natl. Acad. Sci., USA, 85, 6949 (1988) etc., glucuronic acid derivatives described in Chem. Lett., 2145 (1989); Biochim. Biophys. Acta, 1148, 77 (1992) etc., polyethylene glycol derivatives described in Biochim. Biophys. Acta, 1029, 91 (1990); FEBS Lett., 268, 235 (1990) and the like. However, the components are not limited to these examples.

The liposome of the present invention can be prepared by any methods known in the field of the art. Examples of the preparation method are described in the references as general review of liposomes, which are mentioned above, as well as in Ann. Rev. Biophys. Bioeng., 9, 467 (1980), "Liopsomes" (Ed. by M. J. Ostro, MARCELL DEKKER, INC.) and the like. Specific examples include, but not limited thereto, the ultrasonication method, ethanol injection method, French press method, ether injection method, cholic acid method, calcium fusion method, freeze and thawing method, reverse phase evaporation method and the like. Size of the liposome of the present invention may be any of those obtainable by the aforementioned methods. Generally, a size in average may be 400 nm or less, preferably 200 nm or less. Structure of the liposome is not particularly limited, and may be unilamellar or multilamellar structure. It is also possible to formulate one or more kinds of appropriate drugs or other contrast media in the liposome.

When the liposomes of the present invention are used as a contrast medium, they can be preferably administered parenterally, more preferably administered intravenously. For example, preparations in the form of an injection or a drip infusion can be provided as powdery compositions in a lyophilized form, and they can be used by being dissolved or resuspended just before use in water or an appropriate solvent (e.g., physiological saline, glucose infusion, buffering solution and the like). When the liposomes of the present invention are used as a contrast medium, the dose can be suitably determined so that an iodine content in the liposomes becomes similar to that of a conventional iodine-containing contrast medium.

Although it is not intended to be bound by any specific theory, it is known that, in vascular diseases such as arteriosclerosis or restenosis after PTCA, vascular smooth muscle cells constituting tunica media of blood vessel abnormally proliferate and migrate into endosporium at the same time to narrow blood flow passages. Although triggers that initiate the abnormal proliferation of normal vascular smooth muscle cells have not yet been clearly elucidated, it is known that migration of macrophages into endosporium and foaming are important factors. It is reported that vascular smooth muscle cells then cause phenotype conversion (from constricted to composite type).

When the liposomes of the present invention are used, the hydrophobic iodine compound can be selectively taken up into the vascular smooth muscle cells abnormally proliferated under influences of foam macrophages. As a result, it becomes possible to conduct imaging with high contrast of a lesion relative to a non-pathological site. Therefore, the contrast medium of the present invention can be suitably used particularly for X-ray radiography of vascular diseases. For example, radiography of arteriosclerotic lesion or restenosis after PTCA can be performed.

Method for imaging is not particularly limited. For example, imaging can be performed by irradiating an X-ray in the same manner as an imaging method using a usual contrast medium for X-ray radiography. Further, it is also possible to perform imaging based on a method of nuclear medicine by forming liposomes using the compound of the present invention containing a radioisotope of iodine and using the liposomes as a contrast medium for scintigraphy. The radioisotope of iodine is not particularly limited. Preferred examples include $^{123}I$ and $^{125}I$. A compound with radioactive labeling can be synthesized by preparing a corresponding non-labeled compound, and then subjecting the resulting compound to a known process described in Appl. Radiat. Isot., 37 (8), 907 (1986) and the like. When the compound of the present invention is a triiodobenzene derivative, it is preferred that at least one of the three iodine atoms on the same benzene is replaced with the radioisotope. More preferably, two or more of the iodine atoms are replaced with radioisotopes, and most preferably, each of three iodine atoms is replaced with the same kind of radioisotope.

EXAMPLES

The present invention will be explained more specifically with reference to the examples. However, the scope of the present invention is not limited to the following examples. The compound numbers used in the following examples correspond to the numbers of the compounds shown above. Structures of compounds mentioned in the examples were verified by NMR spectra.

Dichloromethane (200 mL) was added with hexadecanedioic acid (10.0 g), 2,4,6-triiodophenol (8.3 g) and N,N-dimethylaminopyridine (0.2 g), further added with ethyldimethylaminopropylcarbodiimide (4.0 g), and stirred at room temperature for one day. After the insoluble solids were removed by filtration, the filtrate was concentrated and purified by silica gel column chromatography to obtain mono(2,4,6-triiodophenyl)hexadecanedioate (3.9 g, yield: 30%). In the same manner as that used for mono(2,4,6-triiodophenyl)hexadecanedioate, mono(2,4,6-triiodophenyl) heptadecanedioate was obtained from heptadecanedioic acid.

Ethanol (70 mL) was added with 12-bromododecanoic acid (4.8 g) and 2,4,6-triiodophenol (9.1 g) and the mixture was refluxed for dissolution. The solution was added with potassium hydroxide (2.2 g) and stirred for 12 hours. The precipitates obtained were separated by filtration, washed with ethanol and added with chloroform and 1 N hydrochloric acid to conduct extraction with chloroform twice. After the organic layer was dried over anhydrous magnesium sulfate, the solvent was removed, and the resulting residue was purified by silica gel column chromatography to obtain 12-(2,4,6-triiodophenoxy)dodecanoic acid (7.0 g, yield: 60%). In the same manner as the synthetic method of 12-(2,4,6-triiodophenoxy)dodecanoic acid, 16-(2,4,6-triiodophenoxy)hexadecanoic acid was synthesized from 16-bromohexadecanoic acid.

Dimethylformamide (DMF, 20 mL) was added with ethyl 7-bromoheptanoate (4.7 g) and 2,4,6-triiodophenol (2.4 g), further added with potassium carbonate (2.1 g) and stirred at room temperature for one day. The reaction solution was added with water and extracted twice with ethyl acetate, and the organic layer was washed three times with water and dried over anhydrous magnesium sulfate. Then, the solvent was removed, and the resulting residue was purified by silica gel column chromatography to obtain ethyl 7-(2,4,6-triiodophenoxy)heptanoate (6.0 g, yield: 96%).

Ethanol (95%, 30 mL) was added with of ethyl 7-(2,4,6-triiodophenoxy)-heptanoate (4.0 g) and the mixture was refluxed for dissolution, and the solution was added with sodium hydroxide (0.5 g) and further refluxed for 1.5 hours. The crystals obtained were separated by filtration, washed with ethanol and added with dichloromethane and 1 N hydrochloric acid to conduct extraction twice with dichloromethane. The organic layer was dried over anhydrous magnesium sulfate, and then the solvent was removed. The resulting residue was purified by silica gel column chromatography to obtain 7-(2,4,6-triiodophenoxy)heptanoic acid (3.4 g, yield: 90%).

In the same manner as that used for 7-(2,4,6-triiodophenoxy)heptanoic acid, 11-(2,4,6-triiodophenoxy)undecanoic acid was obtained from methyl 11-bromoundecanoate.

Dichloromethane (20 mL) was added with methyl 9-hydroxynonanoate (2.1 g) and pyridine (1.8 g), stirred at 0° C., added with methanesulfonyl chloride (1.3 mL), gradually warmed to room temperature and stirred for one day. The reaction solution was added with water and then extracted twice with dichloromethane. The resulting organic layer was washed with 1 N hydrochloric acid and saturated sodium hydrogencarbonate solution. The organic layer was dried over anhydrous sodium sulfate, and then the solvent was removed. The resulting residue was purified by silica gel column chromatography to obtain methyl 9-(methanesulfonyloxy)nonanoate (2.1 g, yield: 68%).

In the same manner as that used for 7-(2,4,6-triiodophenoxy)heptanoic acid, 9-(2,4,6-triiodophenoxy)nonanoic acid was obtained by using methyl 9-(methanesulfonyloxy) nonanoate.

Methanol (150 mL) was added with 15-pentadecalactone (25.6 g), further added with 28% sodium methoxide solution (50 mL) and refluxed for 3 hours. The reaction solution was added with 1 N hydrochloric acid and extracted three times with ethyl acetate. The organic layer was washed with saturated brine and dried over anhydrous magnesium sulfate, and the solvent was removed to obtain methyl 15-hydroxypentadecanoate (28.5 g, yield: 98%).

In the same manner as that used for 9-(2,4,6-triiodophenoxy)nonanoic acid, 15-(2,4,6-triiodophenoxy)pentadecanoic acid was obtained by using methyl 15-hydroxypentadecanoate.

According to the method described in Synth. Commun., 17, 1339 (1987), monomethyl tridecanedioate was obtained by using tridecanedioic acid. Further, according to the method described in Aust. J. Chem., 48, 1893, (1995), methyl 13-hydroxytridecanoate was obtained by using monomethyl tridecanedioate.

In the same manner as that used for 9-(2,4,6-triiodophenoxy)nonanoic acid, 13-(2,4,6-triiodophenoxy)tridecanoic acid was obtained by using methyl 13-hydroxytridecanoate.

In the same manner as that used for 13-(2,4,6-triiodophenoxy)tridecanoic acid, 14-(2,4,6-triiodophenoxy)tetradecanoic acid was obtained by using tetradecanedioic acid.

In the same manner as that used for 13-(2,4,6-triiodophenoxy)tridecanoic acid, 20-(2,4,6-triiodophenoxy)eicosanoic acid was obtained by using eicosanedioic acid.

According to the method described in Arch. Pharm. (Weinheim) 328, 271 (1995), addition of two carbon atoms was performed to 15-(2,4,6-triiodophenoxy)pentadecanoic acid by using diethyl malonate to obtain 17-(2,4,6-triiodophenoxy)heptadecanoic acid.

In the same manner as that used for 17-(2,4,6-triiodophenoxy)heptadecanoic acid, 19-(2,4,6-triiodophenoxy)nanodecanoic acid was obtained by using 17-(2,4,6-triiodophenoxy)heptadecanoic acid.

In the same manner as that used for 17-(2,4,6-triiodophenoxy)heptadecanoic acid, 21-(2,4,6-triiodophenoxy)heneicosanoic acid was obtained by using 19-(2,4,6-triiodophenoxy)nanodecanoic acid.

According to the method described in J. Med. Chem., 29 (12), 2457, (1986), 1,3-diacylglycerol compounds were obtained by using the obtained triiodophenoxyalkylcarboxylic acids.

The aforementioned 1,3-diacylglycerol compound (1.1 mmol) was dissolved in dichloromethane (15 ml) and added with morpholinoacetic acid (0.24 g) synthesized according to the method described in J. Mol. Struct., 560 (1-2), 261 (2001) and dimethylaminopyridine (15 mg), further added with hydrochloride of ethyl-3-dimethylaminopropylcarbodiimide (0.42 g) and stirred at room temperature for one day. The reaction solution was concentrated and purified by silica gel column chromatography to obtain Compound 1A-1-3 (1.60 g, yield: 97%).

1A-1-3:

$^1$H-NMR (300 MHz, CDCl$_3$) δ: 8.05 (4H, s) 5.35-5.28 (1H, m) 4.33 (2H, dd) 4.16 (2H, dd) 3.93 (4H, t) 3.79-3.72 (4H, m) 3.23 (2H, s) 2.63-2.56 (4H,m) 2.31 (4H, t) 1.89 (4H, quin) 1.70-1.48 (8H, m) 1.43-1.20 (20H, m)

In the same manner as that used for Compound 1A-1-3, Compounds 1A-3 were obtained by using 3-morpholinopropanoic acid, 4-morpholinobutanoic acid, 5-morpholinopentanoic acid and 6-morpholinohexanoic acid synthesized according to the method described in J. Mol. Struct., 560 (1-2), 261 (2001) and the 1,3-diacylglycerol compound.

1A-3-1:

$^1$H-NMR (300 MHz, CDCl$_3$) δ: 8.05 (4H, s) 5.32-5.24 (1H, m) 4.30 (2H, dd) 4.18 (2H, dd) 3.92 (4H, t) 3.72-3.65 (4H, m) 2.69 (2H, t) 2.52 (2H, t) 2.48-2.42 (4H,m) 2.32 (4H, t) 1.89 (4H, quin) 1.70-1.48 (8H, m) 1.43-1.20 (20H, m)

1A-3-2:

$^1$H-NMR (300 MHz, CDCl$_3$) δ: 8.05 (4H, s) 5.28-5.22 (1H, m) 4.31 (2H, dd) 4.15 (2H, dd) 3.92 (4H, t) 3.72-3.67 (4H, m) 2.46-2.39 (4H, m) 2.39 (2H, t) 2.35 (2H, t) 2.32 (4H, t) 1.89 (4H, quin) 1.81 (4H, quin) 1.70-1.48 (8H, m) 1.43-1.20 (20H, m)

1A-3-3:

$^1$H-NMR (300 MHz, CDCl$_3$) δ:8.05 (4H, s) 5.30-5.22 (1H, m) 4.30 (2H, dd) 4.15 (2H, dd) 3.92 (4H, t) 3.75-3.67 (4H, m) 2.45-2.28 (12H, m) 1.89 (4H, quin) 1.72-1.48 (12H, m) 1.43-1.20 (20H, m)

1A-3-4:

$^1$H-NMR (300 MHz, CDCl$_3$) δ: 8.05 (4H, s) 5.32-5.22 (1H, m) 4.30 (2H, dd) 4.15 (2H, dd) 3.94 (4H, t) 3.77-3.67 (4H, m) 2.49-2.28 (12H, m) 1.89 (4H, quin) 1.72-1.48 (14H, m) 1.43-1.20 (20H, m)

Morpholine (8.9 g) and succinic anhydride (10.1 g) were dissolved in ethyl acetate (50 mL) and refluxed for 2 hours, and then the solvent was evaporated to obtain a crude product of monomorpholinosuccinic acid. By using the resulting crude product and the 1,3-diacylglycerol compound, Compound 1A-4-1 was obtained in the same manner as that used for Compound 1A-1-3.

1A-4-1:

$^1$H-NMR (300 MHz, CDCl$_3$) δ: 8.05 (4H, s) 5.30-5.22 (1H, m) 4.31 (2H, dd) 4.17 (2H, dd) 3.93 (4H, t) 3.72-356 (6H, m) 3.49 (2H, t) 2.73-2.58 (4H, m) 2.32 (4H, t) 1.89 (4H, quin) 1.70-1.48 (8H, m) 1.43-1.20 (20H, m)

Succinic anhydride (0.15 g) was dissolved in the 1,3-diacylglycerol compound (1.0 mmol) and dichloromethane (20 ml), added with pyridine (0.13 g) and dimethylaminopyridine (11 mg) and refluxed. The reaction solution was concentrated and purified by silica gel column chromatography to obtain Compound 1A-4-4 (0.25 g, yield: 17%).

1A-4-4:

$^1$H-NMR (300 MHz, CDCl$_3$) δ: 8.05 (4H, s) 5.32-5.24 (1H, m) 4.31 (2H, dd) 4.17 (2H, dd) 3.93 (4H, t) 2.72-2.61 (4H, m) 2.32 (4H, t) 1.89 (4H, quin) 1.70-1.48 (8H, m) 1.43-1.20 (20H, m)

Compound 1A-4-2 was obtained in the same manner as that used for Compound 1A-1-3 by using Compound 1A-4-4 and 25% aqueous ammonia.

1A-4-2:

$^1$H-NMR (300 MHz, CDCl$_3$) δ: 8.05 (4H, s) 5.61 (1H, brs) 5.35-5.20 (2H, m) 4.32 (2H, dd) 4.18 (2H, dd) 3.93 (4H, t) 2.70 (2H, t) 2.53 (2H, t) 2.32 (4H, t) 1.89 (4H, quin) 1.70-1.48 (8H, m) 1.43-1.20 (20H, m)

Compound 1A-4-3 was obtained according to the method described in Med. Chem., 40, 3381 (1997) by using Compound 1A-4-4.

1A-4-3:

hu 1H-NMR (300 MHz, CDCl$_3$) δ: 8.05 (4H, s) 5.35-5.22 (1H, m) 4.32 (2H, dd) 4.18 (2H, dd) 3.93 (4H, t) 3.05 (3H, s) 2.95 (3H, s) 2.75-2.59 (4H, m) 2.32 (4H, t) 1.89 (4H, quin) 1.70-1.48 (8H, m) 1.43-1.20 (20H, m)

Compound 1A-4-5 was obtained in the same manner as that used for Compound 1A-4-2 by using Compound 1A-4-4 and triethylene glycol monoethyl ether.

1A-4-5:

$^1$H-NMR (300 MHz, CDCl$_3$) δ: 8.05 (4H, s) 5.32-5.24 (1H, m) 4.31 (2H, dd) 4.40-4.34 (2H, m) 4.17 (2H, dd) 3.93 (4H, t) 3.76-3.60 (10H, m) 3.56 (2H, q) 2.70-2.60 (4H, brs) 2.32 (4H, t) 1.89 (4H, quin) 1.70-1.48 (8H, m) 1.43-1.20 (23H, m)

Cis-1,3-O-benzylideneglycerol (5.10 g) was dissolved in tetrahydrofuran (15 ml) and stirred at 0° C. The solution was slowly added with 60% sodium hydride (1.24 g), warmed to room temperature with stirring and further stirred for 30 minutes. The reaction solution was cooled to 0° C. again, added with chloroacetylmorpholine (6.2 g) dissolved in tetrahydrofuran (5 ml) and stirred at room temperature to for 1 hour. The reaction solution was added with water and extracted twice with ethyl acetate, and the resulting organic layer was washed once with saturated brine. The organic layer was dried over anhydrous magnesium sulfate, and the solvent was removed to obtain colorless crystals of the target substance (4.4 g, yield: 50%).

The crystals obtained above (1.3 g) were added with methanol (40 ml) and 10% palladium carbon (0.1 g) and warmed to 40° C. under a hydrogen atmosphere (41 kg/cm$^2$) for 8 hours. The reaction solution was filtered by using Cerite, and the filtrate was washed with methanol. The solvent of the resulting solution was removed to obtain the target diol as a crude product (0.89 g, yield: 100%).

Compound 1A-5-1 was obtained according to the method described in J. Med. Chem., 29 (12), 2457 (1986) by using the above diol and the synthesized triiodophenoxyalkylcarboxylic acid.

1A-5-1:

$^1$H-NMR (300 MHz, CDCl$_3$) δ: 8.05 (4H, s) 4.29 (2H, s) 4.28 (2H, dd) 4.15 (2H, dd) 3.92 (4H, t) 3.90-3.82 (1H, m) 3.72-3.63 (4H, m) 3.64-3.58 (2H, m) 3.53-3.47 (2H, m) 2.33 (4H, t) 1.89 (4H, quin) 1.70-1.48 (8H, m) 1.43-1.20 (20H, m)

Compound 1A-5-3 was obtained in the same manner as that used for Compound 1A-5-1 by using N,N-dimethylchloroacetic acid amide.

1A-5-3:

$^1$H-NMR (300 MHz, CDCl$_3$) δ: 8.05 (4H, s) 4.29 (2H, s) 4.28 (2H, dd) 4.18 (2H, dd) 3.92 (4H, t) 3.90-3.82 (1H, m) 3.00 (3H, s) 2.96 (3H, s) 2.33 (4H, t) 1.89 (4H, quin) 1.70-1.48 (8H, m) 1.43-1.20 (20H, m)

A t-butyl protected Compound 1A-5-4 was obtained in the same manner as that used for Compound 1A-5-1 by using t-butyl bromoacetate. The above protected compound was dissolved in dichloromethane (15 ml), added with trifluoroacetic acid (2 ml) and stirred at room temperature for one day. The reaction solution was added with water and chloroform for extraction three times, and then the resulting organic layer was dried over sodium sulfate. The solvent was removed, and the residue was purified by silica gel column chromatography to obtain Compound 1A-5-4 (0.8 g, yield: 26%).

1A-5-4:

$^1$H-NMR (300 MHz, CDCl$_3$) δ: 8.05 (4H, s) 4.32 (2H, dd) 4.27 (2H, s) 4.13 (2H, dd) 3.92 (4H, t) 3.90-3.82 (1H, m) 2.37 (4H, t) 1.90 (4H, quin) 1.70-1.48 (8H, m) 1.43-1.20 (20H, m)

Compound 1A-5-2 was obtained in the same manner as that used for Compound 1A-4-2 by using Compound 1A-5-4. In this reaction, Compound 1A-5-10 and Compound 1A-5-11 were also obtained.

1A-5-2:

$^1$H-NMR (300 MHz, CDCl$_3$) δ: 8.05 (4H, s) 6.76 (1H, bs) 5.46 (1H, bs) 4.29 (2H, dd) 4.14 (2H, dd) 4.12 (2H, s) 3.92 (4H, t) 3.85-3.76 (1H, m) 2.34 (4H, t) 1.89 (4H, quin) 1.70-1.48 (8H, m) 1.43-1.20 (20H, m)

1A-5-10:

$^1$H-NMR (300 MHz, CDCl$_3$) δ: 9.35 (1H, bs) 8.05 (4H, s) 4.68 (2H, s) 4.28 (2H, dd) 4.22 (2H, dd) 3.93 (4H, t) 3.90-3.80 (1H, m) 3.67 (2H, t) 3.25 (2H, dq) 2.34 (4H, t) 2.29 (2H, t) 2.22 (6H, s) 1.89 (4H, quin) 1.82 (2H, quin) 1.70-1.48 (8H, m) 1.43-1.20 (20H, m)

1A-5-11:

$^1$H-NMR (300 MHz, CDCl$_3$) δ: 9.00 (1H, bs) 8.05 (4H, s) 4.51 (2H, s) 4.31 (2H, dd) 4.22 (2H, dd) 3.93 (4H, t) 3.93-3.83 (1H, m) 3.68 (2H, q) 3.36 (2H, q) 2.41 (2H, t) 2.34 (4H, t) 2.28 (6H, s) 1.89 (4H, quin) 1.77 (2H, quin) 1.70-1.48 (8H, m) 1.43-1.20 (20H, m)

Compound 1A-6-3 was obtained in the same manner as that used for Compound 1A-1-3 by using N,N-dimethylglycine.

1A-6-3:

$^1$H-NMR (300 MHz, CDCl$_3$) δ: 8.05 (4H, s) 5.40-5.30 (1H, m) 4.33 (2H, dd) 4.16 (2H, dd) 3.93 (4H, t) 3.22 (2H, s) 2.38 (6H, s) 2.33 (4H, t) 1.89 (4H, quin) 1.70-1.48 (8H, m) 1.43-1.20 (20H, m)

(R)-(−)-4-(4-Methoxybenzyloxymethyl)-2,2-dimethyl-1,3-dioxolane (1.5 g) was dissolved in tetrahydrofuran (10 ml) and stirred at 0° C. The reaction solution was slowly added with 60% sodium hydride (0.49 g), warmed to room temperature with stirring and further stirred for 30 minutes. The reaction solution was cooled to 0° C. again, added with ethyl bromoacetate (2.9 g) dissolved in tetrahydrofuran (3 ml) and stirred at room temperature for 1 hour. The reaction solution was added with a saturated ammonium chloride solution and extracted twice with ethyl acetate, and the resulting organic layer was washed once with saturated brine. The organic layer was dried over anhydrous magnesium sulfate, and the solvent was removed. The residue was purified by silica gel column chromatography to obtain colorless oil (1.9 g, yield: 75%).

The above oil (1.0 g) was dissolved in ethanol (10 ml), added with water (20 ml) and sodium hydroxide (0.22 g) and refluxed by heating for 1 hour. The reaction solution was cooled to room temperature, then adjusted to pH 1 to 2 using 1 N hydrochloric acid and extracted three times with chloroform. The extract was dried over anhydrous magnesium sulfate, and the solvent was removed to obtain the target carboxylic acid as colorless oil (0.5 g, yield: 62%). An acetonide protected Compound 1A-6-8 was obtained in the same manner as that used for Compound 1A-1-3 using the above carboxylic acid. Furthermore, a deprotection reaction was performed in the same manner as that used for Compound 1A-5-4 to obtain Compound 1A-6-8.

1A-6-8:

$^1$H-NMR (300 MHz, CDCl$_3$) δ: 8.05 (4H, s) 5.40-5.30 (1H, m) 4.36 (2H, dd) 4.17 (2H, dd) 4.16 (2H, s) 3.93 (4H, t) 3.95-3.85 (1H, m) 3.75-3.50 (4H, m) 2.33 (4H, t) 1.89 (4H, quin) 1.70-1.48 (8H, m) 1.43-1.20 (20H, m)

Compound 1A-6-9 was obtained in the same manner as that used for Compound 1A-6-8 using cis-1,3-O-benzylideneglycerol.

1A-6-9:

$^1$H-NMR (300 MHz, CDCl$_3$) δ: 8.05 (4H, s) 5.38-5.29 (1H, m) 4.38 (2H, dd) 4.30 (2H, s) 4.16 (2H, dd) 3.93 (4H, t) 3.75-3.65 (4H, m) 3.57 (1H, quin) 2.68 (2H, bs) 2.33 (4H, t) 1.89 (4H, quin) 1.70-1.48 (8H, m) 1.43-1.20 (20H, m)

Triethylene glycol monoethyl ether (2.0 g) was dissolved in tetrahydrofuran (10 ml) and added with tosyl chloride (3.3 g). The reaction solution was cooled to 0° C., added with triethylamine (3.2 ml) and stirred at 0° C. for 1 hour and at room temperature for one day. The reaction solution was added with 1 N hydrochloric acid and ethyl acetate and extracted twice with ethyl acetate. Then, the organic layer was dried over anhydrous sodium sulfate, and the solvent was removed. The residue was purified by silica gel column chromatography to obtain the target tosyl compound (3.1 g, yield: 81%).

Compound 1A-7-3 was obtained in the same manner as that used for Compound 1A-5-1 by using the aforementioned tosyl compound.

1A-7-3:

$^1$H-NMR (300 MHz, CDCl$_3$) δ: 8.05 (4H, s) 4.20 (2H, dd) 4.14 (2H, dd) 3.93 (4H, t) 3.82-3.72 (3H, m) 3.68-3.56 (10H, m) 3.53 (2H, q) 2.32 (4H, t) 1.89 (4H, quin) 1.70-1.48 (8H, m) 1.43-1.20 (23H, m)

2-(Cis-1,3-O-benzylideneglyceroyl)ethanol was synthesized by the method described in Arch. Pharm. (Weinheim), 328, 271 (1995). This compound was introduced with a t-butyldimethylsilyl (TBS) protective group according to the method described by T. W. Green & P. G. M. Wuts in Protecting Groups in Organic Synthesis (John Wiley & Sons, Inc.), and a TBS protected Compound 1A-7-5 was obtained in the same manner as that used for Compound 1A-5-1. Furthermore, the TBS group was removed according to the method described in the aforementioned Protecting Groups in Organic Synthesis to obtain Compound 1A-7-5.

1A-7-5:

$^1$H-NMR (300 MHz, CDCl$_3$) δ: 8.05 (4H, s) 4.28 (2H, dd) 4.18 (2H, dd) 3.93 (4H, t) 3.84-3.75 (1H, m) 3.72 (4H, bs) 2.37 (4H, t) 1.90 (4H, quin) 1.70-1.48 (8H, m) 1.43-1.20 (20H, m)

A compound of (S)-(+)-4-(4-methoxybenzyloxymethyl)-2,2-dimethyl-1,3-dioxolane wherein 1-hydroxyl group was substituted with cis-1,3-O-benzylideneglycerol was synthesized according to the method described in Eur. J. Org. Chem., 5, 875 (2001). By using this compound, an acetonide protected Compound 1A-7-6 was obtained in the same manner as that used for Compound 1A-5-1. The protected compound was deprotected in the same conditions used for the deprotection reaction of Compound 1A-5-4 to obtain Compound 1A-7-6.

1A-7-6:
$^1$H-NMR (300 MHz, CDCl$_3$) δ: 8.05 (4H, s) 4.29 (2H, ddd) 4.10 (2H, dd) 3.93 (4H, t) 3.88-3.58 (6H, m) 2.33 (4H, t) 1.89 (4H, quin) 1.70-1.48 (8H, m) 1.43-1.20 (20H, m)

Sodium hydride (0.8 g) was added with DMF (5 mL) and tetrahydrofuran (THF, 20 mL) and stirred at 0° C. The reaction solution was added dropwise with a solution of (S)-(+)-2,2-dimethyl-1,3-dioxolane-4-methanol (2.4 g) in a mixture of DMF (3 mL) and THF (3 mL) and stirred at 0° C. for 1 hour. The reaction solution was added with 4-methoxybenzyl chloride (2.8 mL) and stirred at room temperature for 3 hours. The reaction solution was added with a saturated ammonium chloride solution and extracted twice with ethyl acetate, and the resulting organic layer was washed four times with water and once with saturated brine. The organic layer was dried over anhydrous magnesium sulfate, and the solvent was removed to obtain a crude product of (S)-(+)-4-(4-methoxybenzyloxymethyl)-2,2-dimethyl-1,3-dioxolane (4.1 g, yield: 89%).

The crude product of (S)-(+)-4-(4-methoxybenzyloxymethyl)-2,2-dimethyl-1,3-dioxolane (4.1 g) was dissolved in methanol (10 mL), added with 1 N hydrochloric acid and stirred at room temperature for one day. The reaction solution was adjusted to pH 6 by addition of saturated aqueous sodium hydrogencarbonate and extracted four times with dichloromethane. The organic layer was dried over anhydrous sodium sulfate, and the solvent was removed. The residue was purified by silica gel column chromatography to obtain (R)-(+)-3-(4-methoxybenzyloxy)-1,2-propanediol (2.4 g, yield: 69%).

A methoxybenzyl protected 1,2-diacylglycerol compound was obtained according to the synthesis method for the aforementioned 1,3-diacylglycerol compound by using (R)-(+)-3-(4-methoxybenzyloxy)-1,2-propanediol and the synthesized triiodophenoxyalkylcarboxylic acid. Further, the methoxybenzyl group was removed according to the method described by T. W. Green & P. G. M. Wuts in Protecting Groups in Organic Synthesis (John Wiley & Sons, Inc.) to obtain a 1,2-diacylglycerol compound.

The synthesized 1,2- and 1,3-diacylglycerol compounds were each dissolved in THF (0.1 M), added with 2-chloro-1,3,2-dioxaphosphorane-2-oxide (2.5 equivalents) and stirred at 0° C. The reaction solution was added with triethylamine (3 equivalents), gradually warmed and stirred at room temperature for one day. After the produced precipitates were removed by filtration, the solvent was removed, and the residue was dissolved in THF (0.2 M). This solution was added with a solution of trimethylamine in acetonitrile (about 20% w/w) and heated at 75° C. for 24 hours under a sealed condition. The produced colorless crystals were separated by filtration and washed with acetonitrile. The resulting crystals were dissolved in chloroform, and the insoluble matters were removed. Then, the solvent was removed, and the residue was recrystallized from chloroform/methanol/ethyl acetate to obtain Compounds 1B-1 and 2B-1.

1B-1-3:
$^1$H-NMR (300 MHz, CDCl$_3$) δ: 8.05 (4H, s) 4.59-4.48 (1H, m) 4.35 (2H, brs) 4.30-4.20 (4H, m) 3.92 (4H, t) 3.83 (2H, brs) 3.39 (9H, s) 2.30 (4H, t) 1.99 (4H, quin) 1.68-1.43 (8H, m) 1.43-1.20 (20H, m)

1B-1-4:
$^1$H-NMR (300 MHz, CDCl$_3$) δ: 8.05 (4H, s) 4.59-4.48 (1H, m) 4.35 (2H, brs) 4.30-4.20 (4H, m) 3.92 (4H, t) 3.83 (2H, brs) 3.39 (9H, s) 2.30 (4H, t) 1.99 (4H, quin) 1.68-1.43 (8H, m) 1.43-1.20 (24H, m)

1B-1-7:
$^1$H-NMR (300 MHz, CDCl$_3$) δ: 8.05 (4H, s) 4.59-4.48 (1H, m) 4.35 (2H, brs) 4.30-4.20 (4H, m) 3.92 (4H, t) 3.83 (2H, brs) 3.39 (9H, s) 2.30 (4H, t) 1.99 (4H, quin) 1.68-1.43 (8H, m) 1.43-1.20 (36H, m)

1B-1-8:
$^1$H-NMR (300 MHz, CDCl$_3$) δ: 8.05 (4H, s) 4.59-4.48 (1H, m) 4.35 (2H, brs) 4.30-4.20 (4H, m) 3.92 (4H, t) 3.83 (2H, brs) 3.39 (9H, s) 2.30 (4H, t) 1.99 (4H, quin) 1.68-1.43 (8H, m) 1.43-1.20 (40H, m)

2B-1-3:
$^1$H-NMR (300 MHz, CDCl$_3$) δ: 8.04 (4H, s) 5.26-5.18 (1H, m) 4.40 (1H, dd) 4.40-4.30 (2H, brs) 4.13 (1H, dd) 4.02-3.90 (2H, m) 3.92 (4H, t) 3.82 (2H, brs) 3.39 (9H, s) 2.30 (4H, m) 1.89 (4H, quin) 1.68-1.43 (8H, m) 1.43-1.20 (20H, m)

By using the synthesized 1,2- and 1,3-diacylglycerol compounds, Compounds 1B-9 and 2B-9 were obtained according to the method described in to J. Org. Chem., 64, 648 (1999).

1B-9-1:
$^1$H-NMR (300 MHz, CDCl$_3$) δ: 8.04 (4H, s) 4.50 (1H, drs) 4.25 (4H, brs) 3.92 (4H, t) 2.38-1.27 (4H, m) 1.88 (4H, quin) 1.62-1.45 (8H, m) 1.45-1.20 (20H, m)

1B-9-2:
$^1$H-NMR (300 MHz, CDCl$_3$) δ: 8.05 (4H, s) 4.75-4.65 (1H, m) 4.33 (2H, dd) 4.23 (2H, dd) 4.20-4.10 (2H, m) 3.92 (4H, t) 3.85-3.54 (3H, m) 2.36 (4H, t) 1.99 (4H, quin) 1.68-1.48(8H, m) 1.43-1.20 (20H, m)

1B-9-3:
$^1$H-NMR (300 MHz, CDCl$_3$&CD$_3$ OD) δ: 8.05 (4H, s) 4.58-4.46 (1H, m) 4.38-4.28 (2H, brs) 4.28-4.19 (4H, m) 4.10-4.03 (1H, m) 3.92 (4H, t) 2.33 (4H, dt) 1.89 (4H, quin) 1.68-1.43 (8H, m) 1.43-1.20 (40H, m)

Test Example 1

Uptake Amount of Iodine Atoms by Vascular Smooth Muscle Cells

Dipalmitoyl-PC (Funakoshi, No. 1201-41-0225) and dipalmitoyl-PS (Funakoshi, No. 1201-42-0237) at the ratio shown below were dissolved in chloroform together with each of the iodine compounds of the present invention in an eggplant-shaped flask according to the method described in J. Med. Chem., 25 (12), 1500 (1982) to form a uniform solution. Then, the solvent was evaporated under reduced pressure to form a thin membrane on the bottom of the flask bottom. This thin membrane was dried in vacuum, then added with an appropriate amount of 0.9% physiological saline (Hikari Pharmaceutical, No. 512) and subjected to ultrasonication (No. 3542 probe type oscillator, Branson, 0.1 mW) for 5 minutes to obtain a uniform liposome dispersion.

The diameters of the liposomes in the resulting dispersion were measured by using WBC analyzer (A-1042, Nihon Kohden). As a result, the diameters were found to be 40 to 65 nm. The liposome preparations mentioned below, which were produced by the above method, were each added to a mixed culture system of vascular smooth muscle cells and macrophage described in International Publication WO 01/82977. The cells were cultured at 37° C. under 5% $CO_2$ for 24 hours, and the amounts of the iodine compounds taken up into the vascular smooth muscle cells were each quantified. The compounds of the present invention can be efficiently taken up by vascular smooth muscle cells, and it is clearly understood that they have superior properties as component lipid of liposomes for contrast medium for X-ray radiography.

TABLE 1

|  | Uptake amount |
| --- | --- |
| PC 50 nmol + PS 50 nmol + 1A-1-3 75 nmol | $49.8 \times 10^{-3}$ nmol/μg protein |
| PC 50 nmol + PS 50 nmol + 1A-4-1 75 nmol | $31.4 \times 10^{-3}$ nmol/μg protein |
| PC 50 nmol + PS 50 nmol + 1A-6-8 75 nmol | $48.6 \times 10^{-3}$ nmol/μg protein |
| PC 50 nmol + PS 50 nmol + 1A-7-3 75 nmol | $41.8 \times 10^{-3}$ nmol/μg protein |
| PC 50 nmol + PS 50 nmol + 1A-7-5 75 nmol | $36.1 \times 10^{-3}$ nmol/μg protein |
| PC 50 nmol + PS 50 nmol + 1A-7-6 75 nmol | $39.8 \times 10^{-3}$ nmol/μg protein |

Test Example 2

X-Ray Radiography of Rat Arteriosclerotic Lesion

Figure 2:
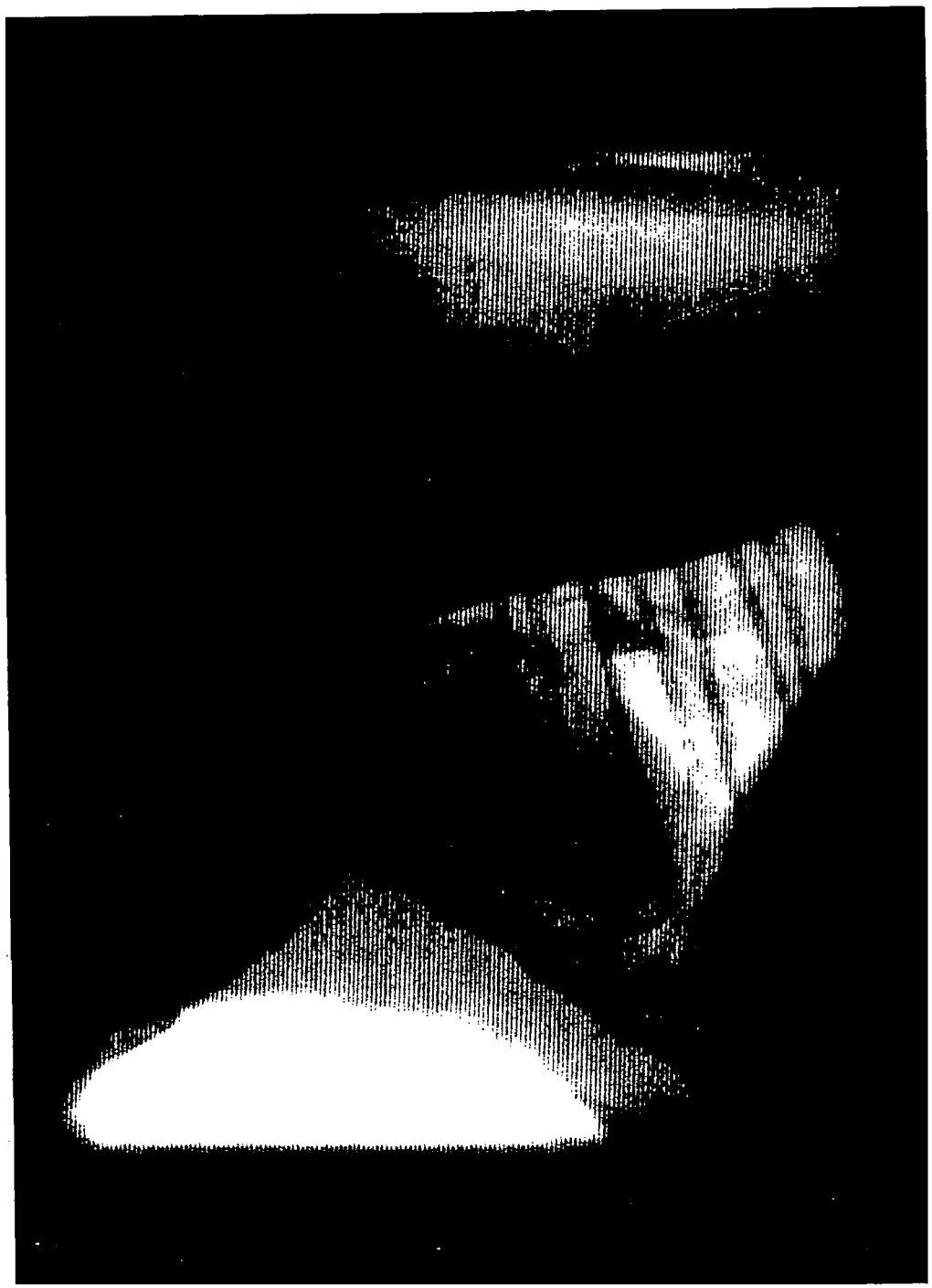
FIG. 2 is a radiographic photograph of a rat immediately after administration of liposomes of the present invention.
Figure 3:
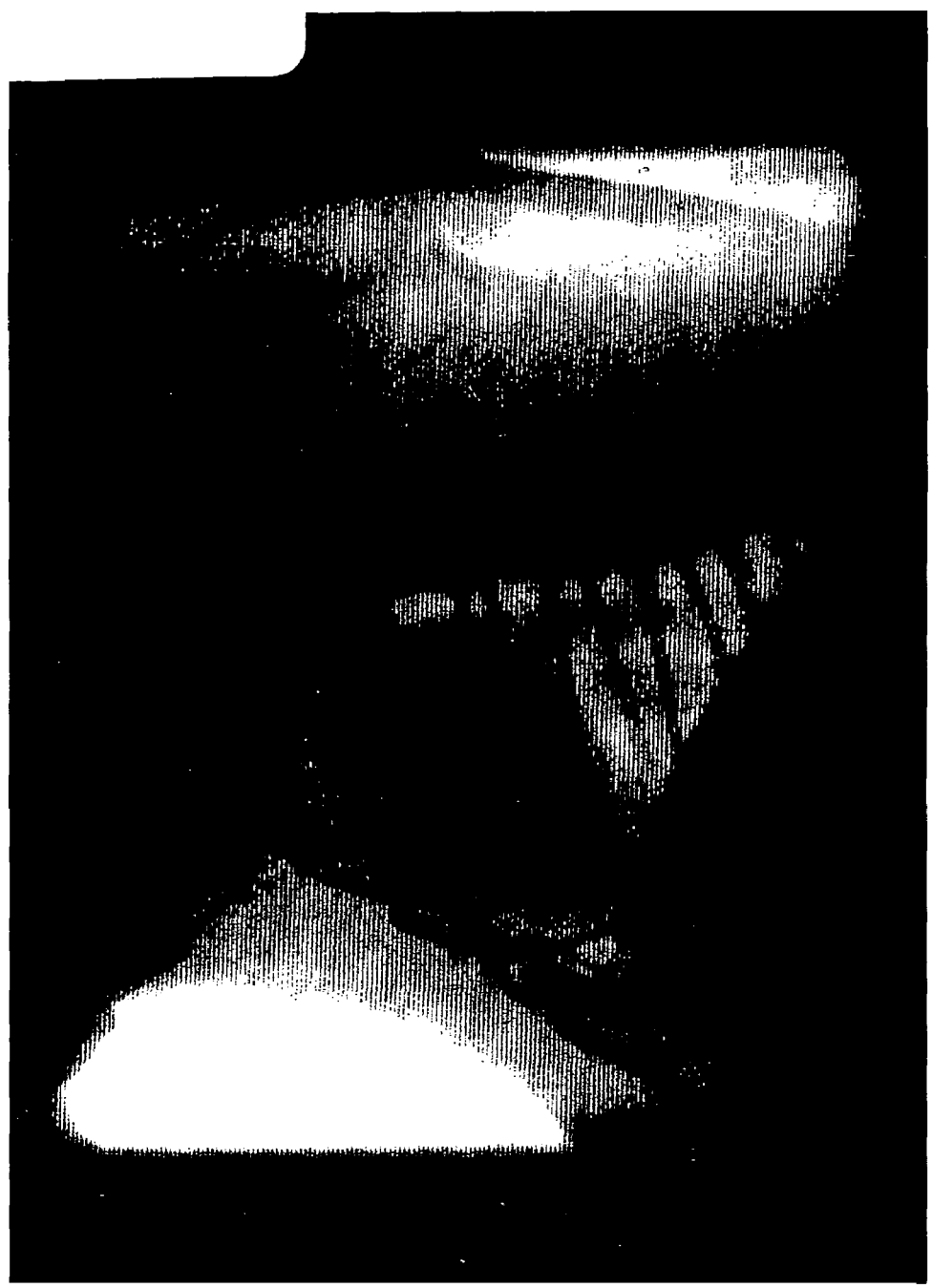
FIG. 3 is a radiographic photograph of an arteriosclerotic lesion of a rat 10 minutes after administration of liposomes of the present invention.
Figure 4:
FIG. 4 is a radiographic photograph of a rat immediately before administration of liposomes of the present invention.
Figure 5:
FIG. 5 is a radiographic photograph of a rat immediately after administration of liposomes of the present invention.
Figure 6:
FIG. 6 is a radiographic photograph of an arteriosclerotic lesion of a rat 1 minute after administration of liposomes of the present invention.
Figure 7:
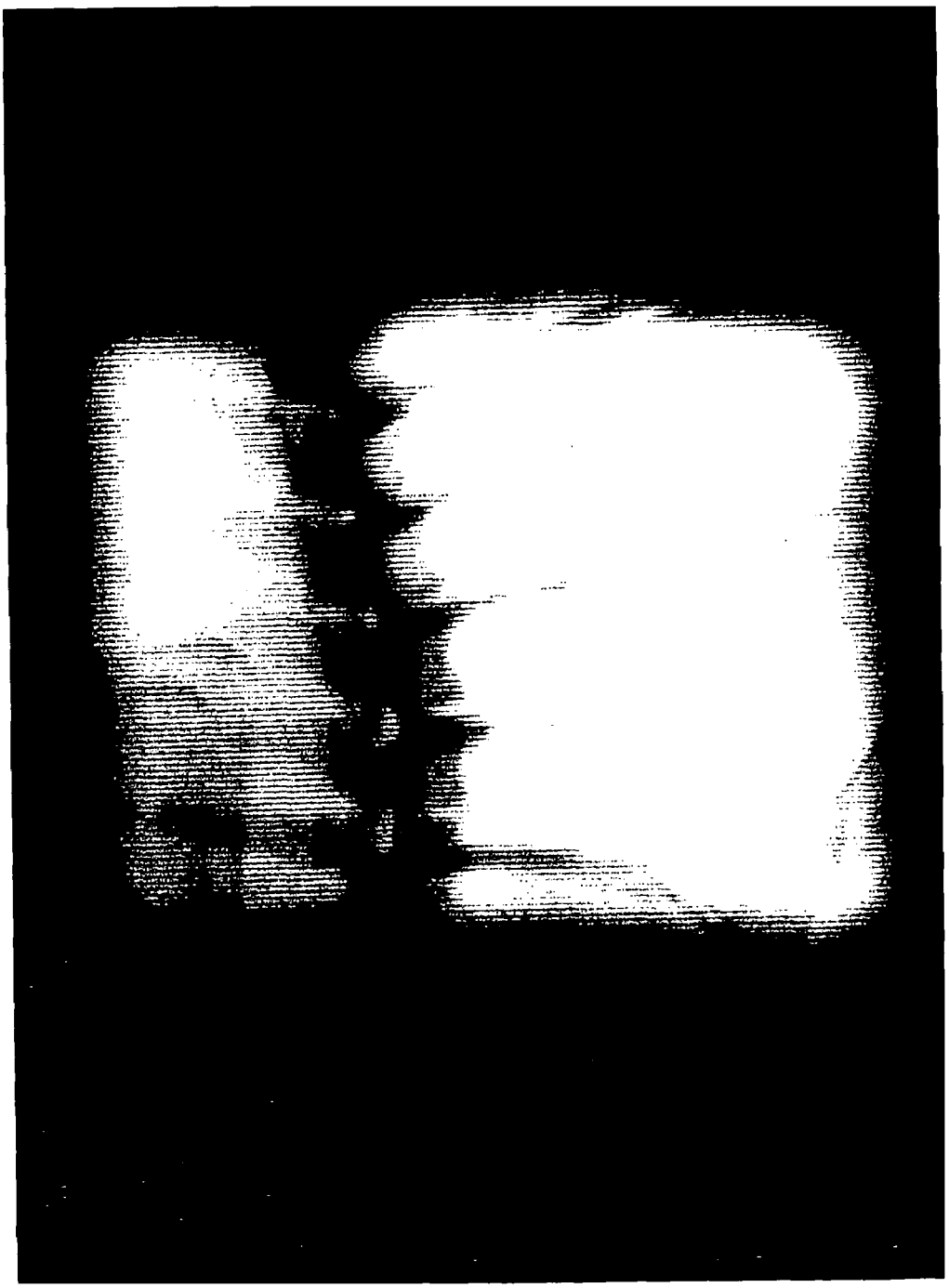
FIG. 7 is a radiographic photograph of a rat 5 minutes after administration of liposomes of the present invention.

According to the method described in Invest. Radiol., 18, 275 (1985), arteriosclerotic lesions were formed in rat aortas. The liposome preparation of 1A-4-1 prepared above was carefully administered to the rats with the formed arteriosclerotic lesions were formed from the cervical vein in an amount of 200 mg/kg. Ten minutes after the administration, clearly contrasted images of the arteriosclerotic lesions were obtained by X-ray radiography. The results are shown in FIGS. 1 to 3.

Test Example 3

Toxicity Test by Continuous Administration for Three Days in Mice

Test Method

Six-week old ICR male mice (Charles River Japan) were purchased, and after quarantine for 1 week, acclimatized in a clean animal cage (air-conditioning: HEPA filter of class 1000, room temperature: 20 to 24° C., humidity: 35 to 60%). Then, in order to obtain an MTD value, a liposome preparation was administered from the caudal vein. The liposome preparation was administered by using physiological saline (Hikari Pharmaceutical) or a glucose solution (Otsuka Pharmaceutical) as a solvent. On the basis of the MTD value obtained, the liposome preparation was administered from the caudal vein every three consecutive days in an amount corresponding to ½ of the MTD value (n=3). The symptoms were observed up to 6 hours after each administration, and autopsy was performed after completion of the administration to examine major organs. As a result, no abnormality was recognized.

TABLE 2

| Compound: | MTD (mg/kg) |
| --- | --- |
| 1A-1-3: | 800 mg/kg |
| 1A-3-2: | 800 mg/kg |
| 1A-3-3: | 1000 mg/kg |
| 1A-3-4: | 1000 mg/kg |
| 1A-4-1: | 1000 mg/kg |
| 1A-4-4: | 800 mg/kg |
| 1A-4-5: | 800 mg/kg |
| 1A-5-1: | 800 mg/kg |
| 1A-5-4: | 800 mg/kg |
| 1A-6-8: | 800 mg/kg |
| 1A-6-9: | 800 mg/kg |

Test Example 4

Neurotoxicity Test in Wistar Rats

Six-week old male Wistar rats (Charles River Japan) were purchased, and after quarantine for 1 week, acclimatized in a clean animal cage (air-conditioning: HEPA filter of class 1000, room temperature: 20 to 24° C., humidity: 35 to 60%). The rats were intraperitoneally administered with pentobarbital (Banyu Pharmaceutical) at a dose of 1 mg/kg, left standing for about 10 to 15 minutes, and then administered with a liposome preparation from the caudal vein in an amount corresponding to ½ of the MTD value obtained in the toxicity test by continual administration for every three days. The liposome preparation was administered by using physiological saline (Hikari Pharmaceutical) or a glucose solution (Otsuka Pharmaceutical) as a solvent. Presence or absence of active movement and convulsion of face and extremities were observed at least up to 4 hours after the administration. None of the compounds of the present invention was found to have neurotoxicity.

TABLE 3

| Compound: | Neurotoxicity (+: present, −: absent) |
| --- | --- |
| 1A-1-3: | (−) |
| 1A-3-3: | (−) |
| 1A-4-1: | (−) |
| 1A-4-4: | (−) |
| 1A-4-5: | (−) |
| 1A-5-1: | (−) |
| 1A-5-4: | (−) |
| 1A-6-8: | (−) |

Test Example 5

Preparation of S9 and Degradation Test

Six-week old male SD rats (Charles River Japan) were purchased and acclimatized for 1 week. After the acclimatization for 1 week, the rats were weighed and bled by decapitation. The liver was extracted and washed three times with chilled 0.15 M KCl. After the washing, wet weight of the liver was determined, and the liver was added with the three-times weight of chilled 0.15 M KCl and placed in a homogenizer. The liver was homogenized, and the homogenate was centrifuged with cooling at 9000 g for 10 minutes. The supernatant obtained was designated S9 and stored below −80° C.

The stored S9 was thawed in running water. The thawed S9 (0.1 ml) was added with 0.4 M $MgCl_2$ (0.02 ml), 1.65 M KCl (0.02 ml) and 0.2 M Na phosphate buffer (pH 7.4, 0.5 ml), added with glucose-6-phosphate (Oriental Yeast), NADPH (Oriental Yeast) and NADH (Oriental Yeast) so as to give a concentration of 4 μM, and added with distilled water to give a total volume of 1 ml (this solution is referred to as "S9 Mix"). S9 Mix (0.1 ml) was added with a test substance so as to give a concentration of 5 μg/ml and shaken at 37° C. under reciprocal movement. The weight of the test substance (unchanged substance) with passage of time in the S9 Mix was measured by HPLC. The test substance was dissolved in dimethyl sulfoxide (Wako Pure Chemical Industry) beforehand. The results are shown as percentage values of the amount of the unchanged substance after 30 minutes based on the amount of the unchanged substance immediately after the addition to S9 Mix, which is taken as 100%. It is clearly understood that the compounds of the present invention were efficiently degraded in the S9 degradation test, and that they have superior properties as lipid components of liposomes for a contrast medium for X-ray radiography.

TABLE 4

| 1A-1-3: 63% | 1A-3-1: 58% | 1A-3-2: 60% |
| 1A-3-3: 64% | 1A-3-4: 63% | 1A-4-1: 59% |
| 1A-4-2: 10% | 1A-4-3: 5% | 1A-4-4: 24% |
| 1A-4-5: 38% | 1A-5-1: 9% | 1A-5-2: 60% |
| 1A-5-3: 52% | 1A-5-4: 20% | 1A-5-10: 56% |
| 1A-5-11: 55% | 1A-6-1: 63% | 1A-6-3: 60% |
| 1A-6-8: 51% | 1A-6-9: 13% | 1A-7-3: 5% |
| 1A-7-5: 11% | 1A-7-6: 21% | |

Test Example 6

Uptake Amount of Iodine Atoms by Vascular Smooth Muscle Cells

In the same manner as in Test Example 1, liposome preparations containing dipalmitoyl-PC (Funakoshi, No. 1201-41-0225) and dipalmitoyl-PS (Funakoshi, No. 1201-42-0237) at the ratio shown below were prepared. The diameters of the liposomes were found to be 40 to 65 nm. The liposome preparations produced by the above method were each added to a mixed culture system of vascular smooth muscle cells and macrophage described in International Publication WO 01/82977. The cells were cultured at 37° C. under 5% $CO_2$ for 24 hours, and the amounts of the iodine compounds taken up into the vascular smooth muscle cells were each quantified. The compounds of the present invention can be efficiently taken up by vascular smooth muscle cells, and it is clearly understood that they have superior properties as component lipid of liposomes for contrast medium for X-ray radiography.

TABLE 5

| | Uptake amount |
|---|---|
| PC 50 nmol + PS 50 nmol + 1B-1-3 75 nmol | $59.8 \times 10^{-3}$ nmol/μg protein |
| PC 50 nmol + PS 50 nmol + 1B-1-7 75 nmol | $35.4 \times 10^{-3}$ nmol/μg protein |
| PC 50 nmol + PS 50 nmol + 1B-1-8 75 nmol | $24.3 \times 10^{-3}$ nmol/μg protein |
| PC 50 nmol + PS 50 nmol + 1B-9-1 150 nmol | $39.6 \times 10^{-3}$ nmol/μg protein |
| PC 50 nmol + PS 50 nmol + 1B-9-3 150 nmol | $33.1 \times 10^{-3}$ nmol/μg protein |
| PC 50 nmol + PS 50 nmol + 2B-1-3 150 nmol | $36.9 \times 10^{-3}$ nmol/μg protein |

TABLE 5-continued

Test Example 7

X-Ray Radiography of Rat Arteriosclerotic Lesion

In the same manner as in Test Example 2, the liposome preparation of 1B-1-3 prepared above was carefully administered from the cervical vein to the rats with the formed arteriosclerotic lesions in an amount of 200 mg/kg. One minute after the administration, clearly contrasted images of arteriosclerotic lesions were obtained by X-ray radiography. The results are shown in FIGS. 4 to 7.

Test Example 8

Toxicity Test by Continuous Administration for Three Days in Mice

Test Method

In the same manner as in Test Example 3, a toxicity test by continual administration for three days was performed in mice. As a result, no abnormal finding was found in the major organs.

TABLE 6

| Compound: | MTD (mg/kg) |
|---|---|
| 1B-1-3: | 2000 mg/kg |
| 1B-1-7: | 800 mg/kg |
| 1B-9-1: | 1000 mg/kg |
| 2B-1-3: | 800 mg/kg |

Test Example 9

Neurotoxicity Test in Wistar Rats

In the same manner as in Test Example 4, the neurotoxicity test using a Wistar rat was performed. As a result, no neurotoxicity was observed for both of the compounds 1B-1-3 and 2B-1-3 of the present invention.

Test Example 10

S9 Degradation Test

S9 Mix was prepared in the same manner as in Test Example 5, and the weight of the test substance (unchanged substance) with passage of time in S9 Mix was measured by HPLC in the same manner as in Test Example 5. It is clearly understood that the compounds of the present invention were efficiently degraded in the S9 degradation test, and that they have superior properties as component lipids of liposomes for a contrast medium for X-ray radiography.

TABLE 7

| 1B-1-3: 4% | 1B-9-1: 0% | 1B-9-2: 31% |
| 1B-9-3: 15% | 2B-1-3: 2% | |

Test Example 11

In vivo Measurement of Test Substance in Liver with Passage of Time

Figure 8:
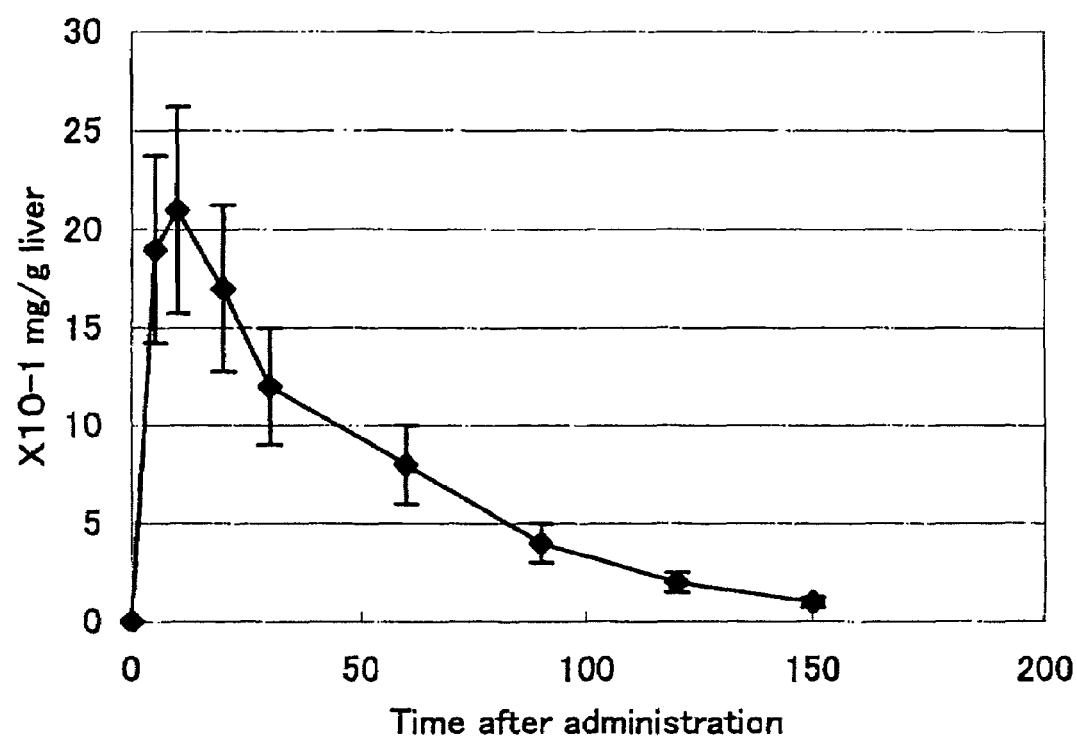
FIG. 8 shows changes of a compound of the present invention (1B-1-3) in the liver in vivo with passage of time.

Six-week old male ICR mice (Charles River Japan) were purchased and acclimatized for 1 week. After the acclimatization for 1 week, the mice were weighed and administered with a test substance from the caudal vein (TERUMO syringe, needle 24 G, TERUMO) at a dose of 200 mg/kg. The test substance was dissolved in DMSO (Wako Pure Chemical Industry) and diluted with mouse blood serum so that the dose (volume) for each mouse did not exceed 200 μL. Each mouse after the administration was sacrificed by dislocation of cervical vertebra. The liver was rapidly extracted and homogenized, and the test substance in the liver was quantified by HPLC. The results are shown in FIG. 8.

When the compounds of the present invention are administered to living bodies (in vivo test), they are degraded and metabolized in the liver, as demonstrated in the S9 degradation test (in vitro test), and give no accumulation in the bodies. Cholesterol iopanoate is known to accumulate in the liver of a living body [J. Med. hem., 25, 1500 (1982)], and compounds that are not hydrolyzed in vivo are disclosed in WO01/93918 for use in radioactive diagnostic imaging. In contrast to those compounds, the compounds of the present invention are degradable in vivo, and therefore, it is clearly understood that they have superior properties as component lipids of liposomes for X-ray radiography contrast medium.

INDUSTRIAL APPLICABILITY

The compounds of the present invention have superior properties as component lipids of liposomes for an X-ray radiography contrast medium, and a vascular lesion can be selectively contrasted by X-ray radiography using the liposomes containing these compounds. Furthermore, the compounds of the present invention have characteristic property that they are metabolized in the liver after imaging of vascular lesions, and give no accumulation in the body.

The invention claimed is:

1. A compound represented by the following general formula (IB) or a salt thereof:

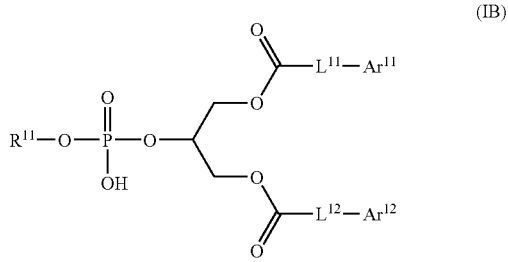

(IB)

wherein $Ar^{11}$ and $Ar^{12}$ each independently represents a hydrogen atom or an aryl group having at least one iodine atom as a substituent, said aryl group being selected from the group consisting of an anthracenyl group, a naphthalenyl group and a phenyl group, and provided that $Ar^{11}$ and $Ar^{12}$ do not simultaneously represent a hydrogen atom;

$L^{11}$ and $L^{12}$ each independently represents a divalent bridging group whose main chain contains 6 or more carbon atoms, selected from the group consisting of $-(CH_2)_n-O-$, $-(CH_2)_m-S-CH_2-$, $-(CH_2)_m-(C=O)O-$, $-(CH_2)_m-(C=O)NH-$, $-(CH_2)_m-O(C=O)-$, $-(CH_2)_m-NH(C=O)-$, $-(CH_2)_p-NH(C=O)-(CH_2)_2-O-$, $-(CH_2)-CH_2-CH=CH-(CH_2)_q-O-$, $-(CH_2)_m-CH(CH_3)-O-$ and $-CH_2CH=CH(CH_2)_8-$, wherein n represents an integer of 6 to 30; m represents an integer of 5 to 29; p represents an integer of 4 to 28; and q represents an integer of 3 to 27;

$R^{11}$ represents a hydrogen atom or an alkyl group containing 2 to 20 carbon atoms and having a functional group containing at least one heteroatom as a substituent, said functional group being selected from the group consisting of an amino group (including a quaternary ammonium group), a hydroxyl group, an alkoxyl group, an acylamino group, an aminocarbonyl group, a carboxyl group, a sulfoxy group, a thiol group, a thioether group, an alkoxycarbonyl group, an aryloxycarbonyl group and an acyloxy group.

2. The compound or a salt thereof according to claim 1, wherein $Ar^{11}$ is a phenyl group having at least three iodine atoms as substituents.

3. The compound or a salt thereof according to claim 1, wherein $Ar^{11}$ and $Ar^{12}$ each independently represents an aryl group having at least one iodine atom as a substituent.

4. The compound or a salt thereof according to claim 1, wherein $Ar^{11}$ and $Ar^{12}$ each independently represents a phenyl group having at least three iodine atoms as substituents.

5. The compound or a salt thereof according to claim 1, wherein $R^{11}$ is a hydrogen atom or an alkyl group containing 2 to 20 carbon atoms that is substituted with a quaternary ammonium group.

6. A liposome containing the compound or a salt thereof according to claim 1 as a membrane component.

7. A liposome containing the compound or a salt thereof according to claim 1 as a membrane component, wherein at least one of the iodine atoms is a radioisotope.

* * * * *